United States Patent
Thor et al.

(10) Patent No.: US 10,086,034 B2
(45) Date of Patent: Oct. 2, 2018

(54) COMPOSITIONS AND METHODS FOR INDUCING URINARY VOIDING AND DEFECATION

(71) Applicant: Dignify Therapeutics, LLC, Research Triangle Park, NC (US)

(72) Inventors: Karl B. Thor, Cary, NC (US); Florenta Aura Kullmann, Pittsburgh, PA (US)

(73) Assignee: Dignify Therapeutics, LLC, Research Triangle Park, NC (US)

( * ) Notice: Subject to any disclaimer, the term of this patent is extended or adjusted under 35 U.S.C. 154(b) by 0 days.

(21) Appl. No.: 15/007,682

(22) Filed: Jan. 27, 2016

(65) Prior Publication Data

US 2016/0175382 A1   Jun. 23, 2016

Related U.S. Application Data

(63) Continuation of application No. PCT/US2014/048953, filed on Jul. 30, 2014.

(60) Provisional application No. 61/860,995, filed on Aug. 1, 2013.

(51) Int. Cl.
| | |
|---|---|
| *A61K 38/08* | (2006.01) |
| *A61K 45/06* | (2006.01) |
| *A61K 38/10* | (2006.01) |
| *A61K 9/00* | (2006.01) |

(52) U.S. Cl.
CPC .............. *A61K 38/08* (2013.01); *A61K 38/10* (2013.01); *A61K 45/06* (2013.01); *A61K 9/0019* (2013.01); *A61K 9/0021* (2013.01); *A61K 9/0056* (2013.01); *A61K 9/0085* (2013.01)

(58) Field of Classification Search
None
See application file for complete search history.

(56) References Cited

U.S. PATENT DOCUMENTS

| | | | |
|---|---|---|---|
| 8,410,281 | B2 | 4/2013 | Ohmoto et al. |
| 2002/0192711 | A1 | 12/2002 | Nestor et al. |
| 2004/0192730 | A1 | 9/2004 | Thor |
| 2005/0089553 | A1 | 4/2005 | Cormier et al. |
| 2006/0293719 | A1 | 12/2006 | Naghavi |
| 2007/0026393 | A1 | 2/2007 | Berlin et al. |
| 2010/0210668 | A1 | 8/2010 | Choi et al. |

FOREIGN PATENT DOCUMENTS

| | | |
|---|---|---|
| JP | H0377899 A | 4/1991 |
| JP | 2010527989 A | 8/2010 |
| WO | 1999064000 A1 | 12/1999 |
| WO | 200006767 A1 | 2/2000 |
| WO | 2006121389 A1 | 11/2006 |
| WO | 2007003411 A2 | 1/2007 |
| WO | 2007012900 A1 | 2/2007 |
| WO | 2011029099 A1 | 3/2011 |

OTHER PUBLICATIONS

Wermuth, Pure and Appl. Chem, 1998, 70, 1129-1143.*
Warner, 2002, Biochemical Pharmacology, 63, 2181-2186.*
Tramontana, 1998, Naunyn-Schmiedeberg's Arch Pharmacol, 358, 293-300.*
Burcher, 2008, The Journal of Pharmacology and Experimental Therapeutics, vol. 324, No. 1, 170-178.*
Pennefather, J.N., et al. : "Tachykinins and tachykinin receptors: a growing family", Life Sci, 2004, vol. 74, No. 12 , pp. 1445-1463.
Catalioto, R.M., et al. : "Independent coupling of the human tachykinin NK2 receptor to phospholipases C and A2 in transfected Chinese hamster ovary cells", Naunyn Schmiedebergs Arch Pharmacol, 1998, vol. 358, No. 4, pp. 395-403.
Cinzia Severini : "The Tachykinin Peptide Family", Pharmacol Rev, 2002, vol. 54, No. 2, pp. 285-322.
Drapeau, G., et al. : "Selective agonists for substance P and neurokinin receptors", Neuropeptides, 1987, vol. 10, No. 1, pp. 43-54.
Rovero, P., et al. : "Structure-activity studies of neurokinin A", Neuropeptides, 1989, vol. 13, No. (4), pp. 263-270.
Regoli, D., et al. : "Neurokinin A. A pharmacological study", Pharmacol Res, 1990, vol. 22, No. (1), pp. 1-14.
Rovero, P., et al. : "A potent and selective agonist for NK-2 tachykinin receptor", Peptides, 1989, vol. 10, No. (3), pp. 593-595.
Saviano, G., et al. : "Conformation-activity relationship of tachykinin neurokinin A (4-10) and of some [Xaa8] analogues", Biochemistry, 1991, vol. 30, No. (42), pp. 10175-10181.
Munekata, E., et al. : "Structure-activity studies of heptapeptide derivatives related to substance P, neurokinin A, B and other tachykinins on smooth muscles", Peptides, 1987, vol. 8, No. (1), pp. 169-173.
David J. S. Guthrie : "Synthesis, monitoring and structure-function studies on some neurokinin A analogues", Biochem Soc Trans, 1990, vol. 18, No. 6, pp. 1323-1325.

(Continued)

*Primary Examiner* — Satyanarayana R Gudibande
(74) *Attorney, Agent, or Firm* — NK Patent Law

(57) ABSTRACT

Methods, pharmaceutical formulations, and kits are provided for using neurokinin 2 receptor agonists to effectuate voluntary "on-demand" voiding of urine and feces in mammals who cannot void without external invasion of the bladder and bowel or those who void involuntarily (i.e., those having urinary and/or fecal incontinence). The pharmaceutical formulations and kits can also be useful for inducing voiding of urine and defecation in mammals that do not have a voiding dysfunction such as, for example, in a person who is comatose and may void unconsciously or in a pet at a convenient location at a specific time. The methods and compositions provide patients with voiding dysfunction control over when and where they void.

26 Claims, 11 Drawing Sheets

Specification includes a Sequence Listing.

(56) References Cited

OTHER PUBLICATIONS

Lovas, S., et al : "Structure-activity relationships of para-substituted Phe analogues of [Nle10]NKA(4-10)", Biochem Soc Trans, 1993, vol. 22, No. 1, p. 5S.
Fisher, L. and J.N. Pennefather : "Structure-activity studies of analogues of neurokinin A mediating contraction of rat uterus", Neuropeptides, 1998, vol. 32, No. (5), pp. 405-410.
Labrou, N.E., et al. : "Structure-activity studies on cysteine-substituted neurokinin A analogs", Peptides, 1999. vol. 20, No. (7), pp. 795-801.
Gembitsky, D.S., et al. : "Importance of the aromatic residue at position 6 of [Nle(10)]neurokinin A(4-10) for binding to the NK-2 receptor and receptor activation", J Med Chem, 1999, vol. 42, No. (15), pp. 3004-3007.
Comis, A. and E. Burcher: "Structure-activity studies at the rat tachykinin NK2 receptor: effect of substitution at position 5 of neurokinin A", J Pept Res, 1999, vol. 53, No. (3), pp. 337-342.
Warner, F.J., et al. : "Structure-activity relationships of neurokinin A (4-10) at the human tachykinin NK(2) receptor: the role of natural residues and their chirality", Biochem Pharmacol, 2001, vol. 61, No. (1), pp. 55-60.
Warner, F.J., R.C. Miller, and E. Burcher : "Human tachykinin NK2 receptor: a comparative study of the colon and urinary bladder", Clin Exp Pharmacol Physiol, 2003, vol. 30, No. (9), pp. 632-639.
Warner, F.J., R.C. Miller, and E. Burcher : "Structure-activity relationship of neurokinin A(4-10) at the human tachykinin NK(2) receptor: the effect of amino acid substitutions on receptor affinity and function", Biochem Pharmacol, 2002, vol. 63, No.(12), pp. 2181-2186.
Deal, M.J., et al. : "Conformationally constrained tachykinin analogues: potent and highly selective neurokinin NK-2 receptor agonists", J Med Chem, 1992, vol. 35, No. (22), pp. 4195-4204.
Burcher, E. et al "Autoradiographic localization of tachykinin and calcitonin gene-related peptide receptors in adult urinary bladder", J Urol, 2000, vol. 163, No. (1), pp. 331-337.
Warner, F.J., et al. : "Circular muscle contraction, messenger signalling and localization of binding sites for neurokinin A in human sigmoid colon", Clin Exp Pharmacol Physiol, 2000, vol. 27, No. (11), pp. 928-933.
Candenas, L., et al. : "Tachykinins and tachykinin receptors: effects in the genitourinary tract", Life Sci, 2005, vol. 76, No. (8), pp. 835-862.
Zeng, X.P., K.H. Moore, and E. Burcher : "Characterization of tachykinin NK2 receptors in human urinary bladder", J Urol, 1995,vol. 153, No. (5), pp. 1688-1692.
Cialdai, C., et al. : "MEN15596, a novel nonpeptide tachykinin NK2 receptor antagonist", Eur J Pharmacol, 2006, vol. 549, vol. (1-3), pp. 140-148.
Palea, S., et al. : "Pharmacological characterization of tachykinin NK2 receptors on isolated human urinary bladder, prostatic urethra and prostate", J Pharmacol Exp Ther, 1996, vol. 277, No. (2), pp. 700-5.v.
Adrian Sculptoreanu : "Neurokinins inhibit low threshold inactivating K+ currents in capsaicin responsive DRG neurons", Exp Neural, 2009, vol. 219, No. 2, pp. 562-573.
Adrian Sculptoreanu : "Neurokinin 2 receptor-mediated activation of protein kinase C modulates capsaicin responses in DRG neurons from adult rats", Eur J Neurosci, Jun. 2008, vol. 27, No. 12, pp. 3171-3181.
Adrian Sculptoreanu : "Protein Kinase C Is Involved in Neurokinin Receptor Modulation of N- and L-Type Ca2 channels in DRG Neurons of the Adult Rat", J Neurophysiol, 2003, vol. 90, No. 1, pp. 21-31.
Adrian Sculptoreanu : "Neurokinins enhance excitability in capsaicin responsive DRG neurons", Exp Neural, 2007, vol. 205, No. 1, pp. 92-100.
John Morrison : "The activation of bladder wall afferent nerves", Experimental Physiology, 1999, vol. 84, No. 1, pp. 131-136.
Monique Saffroy : "Presence of NK2 binding sites in the rat brain", Journal of Neurochemistry, 2001, vol. 79, No. 5, pp. 985-996.
L. Templeman : "Investigation of neurokinin-2 and -3 receptors in the human and pig bladder", BJU Int, 2003, vol. 92, No. 7, pp. 787-792.
Sellers, D.J., et al. : "Depressed contractile responses to neurokinin A in idiopathic but not neurogenic overactive human detrusor muscle", Eur Urol, 2006, vol. 49, No. (3), pp. 510-518.
Giuliani, S., et al. : "Characterization of the tachykinin neurokinin-2 receptor in the human urinary bladder by means of selective receptor antagonists and peptidase inhibitors", J Pharmacol Exp Ther, 1993, vol. 267, No. (2), pp. 590-595.
Teresa Quinn : "Mechanisms of neurokinin A- and substance P-induced contractions in rat detrusor smooth muscle in vitro", BJU Int, 2004, vol. 94, No. 4, pp. 651-657.
Michiko Shinkai : "Characterisation of Tachykinin Receptors in Urinary Bladder from Guinea Pig", Jpn J Pharmacol, 1990, vol. 54, No. 2, pp. 241-243.
P Sadananda : "Contractile properties of the pig bladder mucosa in response to neurokinin A: a role for myofibroblasts?", British Journal of Pharmacology, 2008, vol. 153, No. 7, pp. 1465-1473.
Tramontana, M., et al. : "Tachykinin NK2 receptors in the hamster urinary bladder: in vitro and in vivo characterization", Naunyn Schmiedebergs Arch Pharmacol, 1998, vol. 358, No. (3), pp. 293-300.
N. Suman-Chauhan : "Pharmacological characterization of tachykinin-stimulated inositol phospholipid hydrolysis in peripheral tissues", Br. J. Pharmacol., 1990, vol. 101, No. 4, pp. 1001-1005.
Naline, E., et al. : "Characterization of neurokinin effects and receptor selectivity in human isolated bronchi", Am Rev Respir Dis, 1989, vol. 140, No. (3), pp. 679-686.
Corboz, M.R., et al. : "Increased blocking activity of combined tachykinin NK1- and NK2-receptor antagonists on tachykinergic bronchomotor responses in the guinea-pig", Auton Autacoid Pharmacol, 2003, vol. 23, No. (1), pp. 79-93.
Burcher, E., et al. : "Characterisation of a novel, selective radioligand, [125I][Lys5,Tyr(I2)7,MeLeu9,Nle10]neurokinin A-(4-10), for the tachykinin NK2 receptor in rat fundus", Eur J Pharmacol, 1993, vol. 233, No. (2-3), pp. 201-207.
Zeng, X.P. and E. Burcher : "Use of selective antagonists for further characterization of tachykinin NK-2, NK-1 and possible "septide-selective" receptors in guinea pig bronchus", J Pharmacol Exp Ther, 1994, vol. 270, No. (3), pp. 1295-1300.
Alexandra Wibberley : "Expression and functional role of Rho-kinase in rat urinary bladder smooth muscle", British Journal of Pharmacology, 2003, vol. 138, No. 5, pp. 757-766.
Maggi, C.A., et al. : "In vivo and in vitro pharmacology of SR 48,968, a non-peptide tachykinin NK2 receptor antagonist", Eur J Pharmacol, 1993, vol. 234, No. (1), pp. 83-90.
Kullmann, F.A., et al. : "Exogenous activation of muscarinic receptors decreases subsequent non-muscarinic bladder contractions in vivo in the female rat", Life Sci, 2013, vol. 92, No.(12), pp. 733-739.
A. Lecci : "Bladder distension and activation of the efferent function of sensory fibres: similarities with the effect of capsaicin", British Journal of Pharmacology, 1998, vol. 124, No. 2, pp. 259-266.
Alessandro Lecci : "Nepadutant Pharmacokinetics and Dose-Effect Relationships as Tachykinin NK2 Receptor Antagonist Are Altered by Intestinal Inflammation in Rodent Models", The Journal of Pharmacology and Experimental Therapeutics, 2001, vol. 299, No. 1, pp. 247-254.
Kullmann, F. A., Zheng, J, Wells, G., McKenna, D., Burgard, E. and Thor, K. (2013) "Excitatory effects of neurokinin 2 and bombesin receptor peptide agonists vivo in urinary tract of rats with voiding dysfunctions." FASEB J 27: (Meeting Abstract Supplement) lb862.
Anneli Hällgren : "Neurokinin A increases duodenal mucosal permeability, bicarbonate secretion, and fluid output in the rat", Am J Physiol, 1997, vol. 273, No. 5 Pt 1, pp. G1077-G1086.
Takahiro Tanaka : "Establishment and validation of a rabbit model for in vivo pharmacodynamic screening of tachykinin NK2 antagonists", Journal of Pharmacological Sciences, 2012, vol. 118, No. 4, pp. 487-495.

(56) References Cited

OTHER PUBLICATIONS

Oh-ishi, T., et al. : "Role of tachykinins and neurokinin receptor subtypes in the regulation of motility of the forestomach and abomasum in conscious sheep", Neuropeptides, 2013, vol. 47, No. (1), pp. 9-18.
Carlo Alberto Maggi : "Tachykinin antagonists and capsaicin-induced contraction of the rat isolated urinary bladder: evidence for tachykinin-mediated cotransmission", Br J Pharmacol, 1991, vol. 103, No. 2, pp. 1535-1541.
Onaga, T., et al. : "Role of tachykinin and neurokinin receptors in the regulation of ovine omasal contractions", Regul Pept, 2012, vol. 173, No. (1-3), pp. 64-73.
Lordal, M., E. Theodorsson, and P.M. Hellstrom : "Tachykinins influence interdigestive rhythm and contractile strength of human small intestine", Dig Dis Sci, 1997, vol. 42, No. (9), pp. 1940-1949.
Mikael Lördal : "A novel tachykinin NK2 receptor antagonist prevents motility-stimulating effects of neurokinin A in small intestine", Br J Pharmacol, 2001 , vol. 134, No. 1, pp. 215-223.
Shore, S.A. and J.M. Drazen : "Relative bronchoconstrictor activity of neurokinin A and neurokinin A fragments in guinea pigs", J Appl Physiol, 1991, vol. 71, No. (2), pp. 452-457.
Shigeji Matsumoto : "Effects of tachykinins on rapidly adapting pulmonary stretch receptors and total lung resistance in anesthetized, artificially ventilated rabbits", J Pharmacol Exp Ther, 1997 , vol. 283, No. 3, pp. 1026-1031.
Joseph e. Sherwood : "Bronchoconstrictor and respiratory effects of neurokinin A in dogs", J Pharmacol Exp Ther, 1997 , vol. 283, No. 2, pp. 788-793.
G Joos : "Effect of inhaled substance P and neurokinin A on the airways of normal and asthmatic subjects", Thorax, 1987 , vol. 42, No. 10, pp. 779-783.
Cheung, D., et al. : "The effect of an inhaled neutral endopeptidase inhibitor, thiorphan, on airway responses to neurokinin A in normal humans in vivo", Am Rev Respir Dis, 1992, vol. 145, No. (6), pp. 1275-1280.
G. F. Joos : "Role of tachykinins in asthma", Allergy, 2000 , vol. 55, No. 4, pp. 321-337.
G.F. Joos : "Dual tachykinin NK1/NK2 antagonist DNK333 inhibits neurokinin A-induced bronchoconstriction in asthma patients", Eur Respir J, 2004 , vol. 23, No. 1, pp. 76-81.
Johan D. Boot : "Effect of an NK1/NK2 receptor antagonist on airway responses and inflammation to allergen in asthma", Am J Respir Crit Care Med, 2007 , vol. 175, No. 5, pp. 450-457.
Schelfhout, V., et al. : "The triple neurokinin-receptor antagonist CS-003 inhibits neurokinin A-induced bronchoconstriction in patients with asthma", Pulm Pharmacol Ther, 2006, vol. 19, No. (6), pp. 413-418.
Gaetano Prosperini : "Beclomethasone dipropionate attenuates airways hyperresponsiveness to neurokinin A and histamine in asthma", Respir Med, 2006 , vol. 100, No. 6, pp. 1006-1012.
T. W. Evans : "Comparison of neurokinin A and substance P on cardiovascular and airway function in man", Br J Clin Pharmacol, 1988 , vol. 25, No. 2, pp. 273-275.
P T Schmidt : "Tachykinins potently stimulate human small bowel blood flow: a laser Doppler flowmetry study in humans", Gut, 2003 , vol. 52, No. 1, pp. 53-56.

Mark Bushfield : "Activation of the micturition reflex by NK2 receptor stimulation in the anaesthetized guinea-pig", Br J Pharmacol , 1995 , vol. 115, No. 6, pp. 875-882.
Lecci, A., S. Giuliani, R. Patacchini and C. A. Maggi : "Evidence against a peripheral role of tachykinins in the initiation of micturition reflex in rats." J Pharmacol Exp Ther, 1993, vol. 264, No. (3), pp. 1327-1332.
Watling, K. J. et al.: "Species variants of tachykinin receptor types", Biochem Soc Trans. Feb. 1994;22(1):118-22.
ISA/US, International Search Report and Written Opinion for PCT Patent Application PCT/US2014/048953, dated Apr. 23, 2015.
European Patent Office, Office Action in European Patent Application No. EP 14 832 175.5 dated Dec. 22, 2017.
European Patent Office, Supplementary European Search Report for European Patent Application No. EP 14 83 2175 dated Jan. 12, 2017.
Carini, F., et al., Tachykinin NK2 receptors and enhancement of cholinergic transmission in the inflamed rat colon: an in vivo motility study, British Journal of Pharmacology, Jan. 1, 2001, ,pp. 1107-1113, XP055327620.
Nakamura, Akihiro, et al., Bidirectional Regulation of Human Colonic Smooth Muscle Contractility by Tachykinin NK2 Receptors, Journal of Pharmacological Sciences, 2011, pp. 106-115. vol. 117.
Tanaka, Takahiro, et al., Effects of TAK-480, a Novel Tachykinin NK2-Receptor Antagonist, on Visceral Hypersensitivity in Rabbits and Ricinoleic Acid-Induced Defecation in Guinea Pigs, Journal of Pharmacological Sciences, 2012, pp. 15-25, vol. 120.
Kerr, Karen P., et al., Tachykinin-induced contraction of the guinea-pig isolated oesophageal mucosa is mediated by NK2 receptors, British Journal of Pharmacology, 2000, pp. 1461-1467, vol. 131.
Kullman, F. Aura, et al., Excitatory effects of bombesin receptors in urinary tract of normal and diabetic rats in vivo, Life Sciences, 2014, pp. 35-44, vol. 100.
Kullman, F. Aura, et al., Functional bombesin receptors in urinary tract of rats and human not of pigs and mice, an in vitro study, Neuropeptides, 2013, pp. 305-313, vol. 47.
Maggi, Carob Alberto, et al., Facilitation of Reflex Micturition by Intravesical Administration of [βAIa8]-Neurokinin A (4-10), a Selective NK-2 Tachykinin Receptor Agonist, The Journal of Urology, Jan. 1991, pp. 184-187, vol. 145.
Evangelista, S., et al., Analogs of Neurokinin A(4-10) Afford Protection Against Gastroduodenal Ulcers in Rats, Peptides, Jul. 31, 1989 pp. 293-297, vol. 11.
J. Clin. Invest., 1990, vol. 85, pp. 170-176.
British Journal of Pharmacology, 1995, vol. 115, pp. 875-882.
The Journal of Pharmacology and Experimental Therapeutics, 2001, vol. 299, No. 1, pp. 247-254.
The Journal of Urology, 1991, vol. 145, pp. 184-187.
The Journal of Urology, 1995, vol. 153, pp. 1688-1692.
Clinical and Experimental Pharmacology and Physiology, 2003, vol. 30, pp. 632-639.
JPO, Office Action for Japanese Patent Application No. 2016-531869, dated Apr. 10, 2018.

* cited by examiner

SEQUENCE LISTING

```
<160> NUMBER OF SEQ ID NOS: 7

<210> SEQ ID NO 1
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Leu at position 6 is methylated at the nitrogen
<220> FEATURE:
<221> NAME/KEY: MISC_FEATURE
<222> LOCATION: (7)..(7)
<223> OTHER INFORMATION: X at position 7 is norleucine

<400> SEQUENCE: 1

Asp Lys Phe Val Gly Leu Xaa
1               5

<210> SEQ ID NO 2
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Met at position 10 has a NH2 group at the
      carboxyl terminus

<400> SEQUENCE: 2

His Lys Thr Asp Ser Phe Val Gly Leu Met
1               5                   10

<210> SEQ ID NO 3
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (10)..(10)
```

<223> OTHER INFORMATION: Met at position 10 has a NH2 group at the
      carboxyl terminus

<400> SEQUENCE: 3

Asp Met His Asp Phe Phe Val Gly Leu Met
1               5                   10

<210> SEQ ID NO 4
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: Met at position 11 has a NH2 group at the
      carboxyl terminus

<400> SEQUENCE: 4

Arg Pro Lys Pro Gln Gln Phe Phe Gly Leu Met
1               5                   10

<210> SEQ ID NO 5
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Met at position 7 has a NH2 group at the
      carboxyl terminus

<400> SEQUENCE: 5

Asp Ser Phe Val Gly Leu Met
1               5

<210> SEQ ID NO 6
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: X at position 5 is a beta alanine
<220> FEATURE:
<221> NAME/KEY: MISC_FEATURE
<222> LOCATION: (7)..(7)
<223> OTHER INFORMATION: Met at at position 7 has a NH2 group at the
      carboxyl terminus

<400> SEQUENCE: 6

Asp Ser Phe Val Xaa Leu Met
1               5

<210> SEQ ID NO 7
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X at position 2 is eitherTyr, Phe, Val, or Ile
<220> FEATURE:
<221> NAME/KEY: MISC_FEATURE

```
<222> LOCATION: (5)..(5)
<223> OTHER INFORMATION: Met at position 5 has a NH2 group at the
      carboxyl terminus

<400> SEQUENCE: 7

Phe Xaa Gly Leu Met
1               5
```

COMPOSITIONS AND METHODS FOR INDUCING URINARY VOIDING AND DEFECATION

CROSS REFERENCE TO RELATED APPLICATIONS

This application is a Continuation application of International Patent Application No. PCT/US2014/48953 filed on Jul. 30, 2014, which claims the benefit of U.S. provisional patent application No. 61/860,995 filed Aug. 1, 2013, the disclosures of which are hereby incorporated by reference in their entireties.

TECHNICAL FIELD

The presently disclosed subject matter relates to methods of using neurokinin receptor agonists and antagonists for inducing urinary voiding and defecation.

BACKGROUND

The inability to eliminate urine and/or feces is a life-threatening condition. The current standard of care for urinary voiding dysfunction requires passage of a clean catheter through the urethra and further into the urinary bladder to facilitate urine flow through the catheter externally. The current standard of care for fecal dysfunction includes digital extraction of feces from the rectum in combination with a diet conducive to stool passage. Some patients receive large volume (1 L) warm water enemas that can require waiting for 30 minutes to an hour while the water and fecal contents are expelled.

Patients with voiding dysfunction may also experience episodes of incontinence, whereby the large volume of urine and/or feces in the bladder and/or bowel are subject to acute increases in intraluminal pressure that force urine and/or feces past the urethral and/or anal sphincters. While accidental voiding has occurred, the void may be incomplete, and the patient remains at risk for urinary tract infections and/or bowel problems.

Voiding dysfunction is extremely prevalent in patients with spinal cord injury, spina bifida, multiple sclerosis, and other conditions involving spinal cord pathology. Voiding dysfunction is also prevalent in subjects with diabetic cystopathy and gastroenteropathy. Voiding dysfunction is also seen in various elderly subjects and is prevalent among the institutionalized.

Existing therapies for urinary voiding dysfunction include either clean intermittent or indwelling catheterization which can result in catheter associated urinary tract infections (CAUTI). CAUTI account for more than 15% of infections reported by acute care hospitals and can lead to complications such as cystitis, pyelonephritis, gram-negative bacteremia, prostatitis, epididymitis, and orchitis in males and, less commonly, endocarditis, vertebral osteomyelitis, septic arthritis, endophthalmitis, and meningitis in all patients. Complications associated with CAUTI cause discomfort to the patient, prolong hospital stay, and increase cost and mortality. Each year, more than 13,000 deaths are associated with UTIs. In addition, persons with SCI (and other CNS damage) often lack the physical ability to catheterize themselves.

Cholinergic agonists such as bethanechol (a muscarinic receptor agonist) and distigmine (an acetylcholinesterase inhibitor) have been used as therapy. However, the efficacy of these compounds is limited and tolerability is low due to severe side effects such as sweating, spasticity, bradycardia, convulsions, hypotension, bronchial constriction (Taylor and Kuchel 2006). Alternative methods have been developed to empty the bladder by preventing the sphincter from closing the urethra, but most of them, including sphincterotomy, sphincter paralysis, and urethral stenting, leave the person incontinent and lead to further complications.

Lower urinary tract disorders including underactive bladder and incontinence greatly affect the quality of life of patients. Voiding dysfunction associated with the inability to completely void the bladder of urine during micturition is a condition affecting the elderly, diabetic, neurogenic (spinal cord injury, spina bifida, multiple sclerosis, stroke patients, traumatic brain injury, Parkinson's, Alzheimer's, ALS), and other patient populations. The condition can arise from impaired contractility of the bladder smooth muscle of myogenic nature, e.g. in the elderly; impaired relaxation of the urethral smooth muscle, e.g. in the elderly; damage of the peripheral nerves (afferents and/or efferents) e.g. in diabetic neuropathy; impaired neuronal control due to injury of the spinal cord or brain, e.g. in spinal cord injury, multiple sclerosis, stroke patients, traumatic brain injury, Parkinson's, Alzheimer's, and other conditions and disorders. This condition can lead to elevated post-void residual urine volumes and symptoms of frequency, nocturia, incontinence, and urinary tract infections.

The International Continence Society refers to the condition of detrusor under activity, defined as a contraction of reduced strength and/or duration, resulting in prolonged bladder emptying and/or failure to achieve complete bladder emptying within a usual time span. It is characterized by the loss of usual sensation of the bladder filling and failure of the detrusor muscle to contract as forcefully as it should, resulting in incomplete bladder emptying. This condition has also been referred to as a hypotonic or flaccid bladder or detrusor hypoactivity. Underactive Bladder Syndrome is a chronic, complex and debilitating disease which affects the urinary bladder with serious consequences. Detrusor underactivity has been found in nearly two-thirds of the incontinent institutionalized elderly. However, the incidence and prevalence of a condition is highly dependent on both definition and available diagnostic tests (Taylor and Kuchel 2006).

Spinal cord injury is the most common injury that profoundly affects voiding and usually results from traffic accidents, sports injuries, but also from infections, vascular disorders, cancers, congenital malformations, polio, tuberculosis, etc. It is estimated that the annual incidence of spinal cord injury (SCI), not including those who die at the scene of the accident, is approximately 40 cases per million population in the U. S. or approximately 12,000 new cases each year. The number of people in the United States who are alive in 2012 who have SCI has been estimated to be approximately 270,000 persons, with a range of 236,000 to 327,000 persons.

For a person with SCI, the direct medical costs associated with urinary tract dysfunction may exceed $8,000 each year, making up a substantial component of the estimated $31,000 to $75,000 annual health care and living expenses of individuals with spinal injury. Furthermore, the loss of control of urinary function alters social relationships and can be personally demoralizing, and it can lead to depression, anger, poor self-image, embarrassment, frustration and can prevent persons from achieving their personal goals.

Following spinal cord injury, the bladder is usually affected in one of two ways. The first is a condition called "spastic" or "reflex" bladder, in which the bladder fills with urine and a reflex automatically triggers the bladder to empty. This usually occurs when the injury is above the T12 level. Individuals with spastic bladder are unable to determine when, or if, the bladder will empty. The second is "flaccid" or "non-reflex" bladder, in which the reflexes of the bladder muscles are absent or slowed. This usually occurs when the injury is below the T12/L1 level. Individuals with flaccid bladder may experience over-distended or stretched bladders and "reflux" of urine through the ureters into the kidneys. Treatment options for these disorders usually include intermittent catheterization, indwelling catheterization, or condom catheterization, but these methods are invasive and frequently inconvenient.

Urinary sphincter muscles may also be affected by spinal cord injuries, resulting in a condition known as "dyssynergia." Dyssynergia involves an inability of urinary sphincter muscles to relax when the bladder contracts, including active contraction in response to bladder contraction, which prevents urine from flowing through the urethra and results in the incomplete emptying of the bladder and "reflux" of urine into the kidneys. Traditional treatments for dyssynergia include medications that have been somewhat inconsistent in their efficacy or surgery.

Injury to spinal cord and/or brain can lead to inability to voluntarily defecate. Currently patients use manual extraction of feces, or in some cases use large volume (1 L) warm water enemas that require sitting on the toilet for 30 minutes to an hour while the water and fecal contents are expelled. In some cases, an irritative "stimulant laxative" is administered intra-rectally, although effects may last hours longer than necessary and cannot be administered on a regular basis. These methods are either performed by the patient, if able to perform them, or by the caregiver. They can be degrading to the self-esteem of patients and can be personally demoralizing, altering social relationships, leading to depression, anger, poor self-image, embarrassment, frustration, etc.

Fecal incontinence is defined as accidental passing of solid or liquid stool or mucus from the rectum. Fecal incontinence includes the inability to hold a bowel movement until reaching a toilet as well as passing stool into one's underwear without being aware of it happening. Fecal incontinence can be upsetting and humiliating. The condition affects ~18 million people in the US.

Constipation is one of the most common forms of gastrointestinal hypomotility disorders. Constipation is one of the most common gastrointestinal complaints in the United States. More than 4 million Americans have frequent constipation, accounting for 2.5 million physician visits a year. Self-treatment of constipation with over-the-counter (OTC) laxatives is by far the most common aid. Around $725 million is spent on laxative products each year in America.

Constipation is common in a number of gastrointestinal tract disorders including but not limited to irritable bowel syndrome, celiac disease or gluten-sensitive enteropathy, megacolon associated with hypothyroidism, pseudo-obstruction of the gastrointestinal tract, colitis, hypomotility of the colon associated with diabetes mellitus, adult onset Hirschsprung's disease, neurological disorders, myopathic disorders, spinal cord injury, Parkinson's disease, jejunal-ileal bypass with secondary megacolon, cancer chemotherapy, critical illness including severe burns and other major stresses, with syndromes of depression, the post-operative state, and other pathological conditions.

Present treatments include: over-the-counter (OTC) laxatives, AMITIZA (lubiprostone which is a chloride channel activator; approved for irritable bowel syndrome with constipation or IBS-C), LINZESS (linaclotide; a guanylatecyclase-C agonist; approved for the treatment of IBS-C and chronic idiopathic cystitis, CIC). However, none of these available medications produce colon contraction and expulsion of feces, rather they increase the fluid in the intestines.

Because existing therapies and treatments for voiding dysfunction are associated with limitations as described above, new therapies and treatments are therefore desirable. The presently disclosed subject matter provides such new therapies and treatments to address these limitations.

SUMMARY

In one embodiment of the presently disclosed subject matter, a method is provided for treating one of urinary voiding and defecation dysfunction in a mammal in need of treatment, which comprises administering on an as-needed basis to the mammal a therapeutically effective amount of an neurokinin 2 receptor (NK2R) agonist or a pharmaceutically acceptable salt thereof, wherein the NK2R agonist or the pharmaceutically acceptable salt thereof, has a rapid onset and a short duration of action, to induce the one or both of urinary voiding and defecation.

In one embodiment of the presently disclosed subject matter, a method is provided for treating one of urinary voiding and defecation dysfunction in a mammal in need of treatment, which comprises administering on an as-needed basis to the mammal a therapeutically effective amount of [Lys5,MeLeu9,Nle10]-NKA(4-10) (SEQ ID NO: 1), or a pharmaceutically acceptable salt thereof, to induce the one or both of urinary voiding and defecation.

In one embodiment of the presently disclosed subject matter, a pharmaceutical formulation is provided for treating one of urinary voiding and defecation dysfunction in a mammal in need of treatment on an as-needed basis, which comprises a therapeutically effective amount of a rapid onset and short acting neurokinin 2 receptor (NK2R) agonist, or a pharmaceutically acceptable salt thereof, and a carrier for administration of the NK2R agonist to the mammal on the as-needed basis.

In one embodiment of the presently disclosed subject matter, a pharmaceutical formulation is provided for treating one of urinary voiding and defecation dysfunction in a mammal in need of treatment on an as-needed basis, which comprises a therapeutically effective amount of [Lys5,MeLeu9,Nle10]-NKA(4-10) (SEQ ID NO: 1), or a pharmaceutically acceptable salt thereof, and a carrier for administration of the [Lys5,MeLeu9,Nle10]-NKA(4-10) (SEQ ID NO: 1) to the mammal on the as-needed basis.

In one embodiment of the presently disclosed subject matter, a packaged kit is provided for a patient to use in the treatment of loss of or decrease in voluntary control of voiding and/or defecation or having urinary and/or fecal incontinence, comprising a pharmaceutical formulation of a therapeutically effective amount of a rapid onset and short acting neurokinin 2 receptor (NK2R) agonist, or a pharmaceutically acceptable salt thereof; a container housing the pharmaceutical formulation during storage and prior to administration; and instructions for carrying out administration in a manner effective to treat the loss or decrease in control and/or the incontinence.

In one embodiment of the presently disclosed subject matter, a packaged kit is provided for a patient to use in the treatment of loss of or decrease in voluntary control of voiding and/or defecation or having urinary and/or fecal incontinence, comprising a pharmaceutical formulation of a therapeutically effective amount of [Lys5,MeLeu9,Nle10]-NKA(4-10) (SEQ ID NO: 1), or a pharmaceutically acceptable salt thereof; a container housing the pharmaceutical formulation during storage and prior to administration; and instructions for carrying out administration in a manner effective to treat the loss or decrease in control and/or the incontinence.

In one embodiment of the presently disclosed subject matter, a packaged kit is provided for a patient to use for treating one of urinary voiding and defecation dysfunction on an as-needed basis, comprising a pharmaceutical formulation of a therapeutically effective amount of a rapid onset and short acting neurokinin 2 receptor (NK2R) agonist, or a pharmaceutically acceptable salt thereof; a container housing the pharmaceutical formulation during storage and prior to administration; and instructions for carrying out administration on the as-needed basis to treat the urinary voiding and/or defecation dysfunction.

In one embodiment of the presently disclosed subject matter, a packaged kit is provided for a patient to use for treating one of urinary voiding and defecation dysfunction on an as-needed basis, comprising a pharmaceutical formulation of a therapeutically effective amount of [Lys5,MeLeu9,Nle10]-NKA(4-10) (SEQ ID NO: 1), or a pharmaceutically acceptable salt thereof; a container housing the pharmaceutical formulation during storage and prior to administration; and instructions for carrying out administration on the as-needed basis to treat the urinary voiding and/or defecation dysfunction.

In one embodiment of the presently disclosed subject matter, a method is provided for inducing one of urinary voiding and defecation in a mammal, which comprises administering on an as-needed basis to the mammal a therapeutically effective amount of an neurokinin 2 receptor (NK2R) agonist or a pharmaceutically acceptable salt thereof, wherein the NK2R agonist or the pharmaceutically acceptable salt thereof, has a rapid onset and a short duration of action, to induce one or both of the urinary voiding and defecation.

In one embodiment of the presently disclosed subject matter, a method is provided for inducing one of urinary voiding and defecation in a mammal, which comprises administering on an as-needed basis to the mammal a therapeutically effective amount of [Lys5,MeLeu9,Nle10]-NKA(4-10) (SEQ ID NO: 1), or a pharmaceutically acceptable salt thereof, to induce one or both of the one of urinary voiding and defecation.

In one embodiment of the presently disclosed subject matter, a method is provided for inducing one of urinary voiding and defecation in a mammal, which comprises: administering on an as-needed basis to the mammal a therapeutically effective amount of a neurokinin 2 receptor (NK2R) agonist or a pharmaceutically acceptable salt thereof, the NK2R agonist having a rapid onset and a short duration of action, to induce the one or both of urinary voiding and defecation; and administering a therapeutically effective amount of a NK2R antagonist, or a pharmaceutically acceptable salt thereof, to terminate at least a majority of the effects of the NK2R agonist after occurrence of the one or both of urinary voiding and defecation, wherein the NK2R antagonist has a duration of action of less than about 4 hours.

BRIEF DESCRIPTION OF THE FIGURES

The foregoing aspects and other features of the invention are explained in the following description, taken in connection with the accompanying drawings.

Figure 11A:
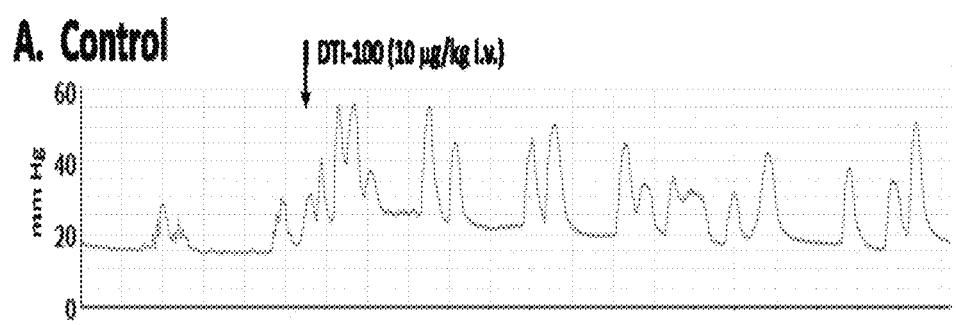
Figure 11B:
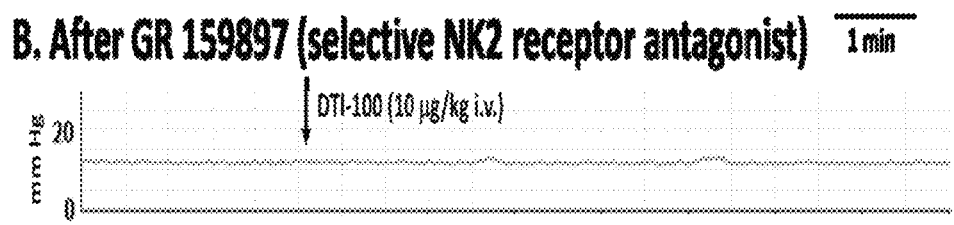

FIGS. 11A-11B are graphs showing the DTI-100 induced increase in colorectal activity (mm Hg) before (A) and after (B) administration of GR159897 (NK2R antagonist) in anesthetized acutely spinalized female rats according to one or more embodiments of the presently disclosed subject matter. The arrows indicate the time at which the DTI-100 (10 µg/kg) was administered and correspond to 5 min after the start of the experiment in (A) and 5 min after administration of GR159897 in (B).

DETAILED DESCRIPTION

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

In one embodiment of the presently disclosed subject matter, a method is provided for treating one of urinary voiding and defecation dysfunction in a mammal in need of treatment, which comprises administering on an as-needed basis to the mammal a therapeutically effective amount of an neurokinin 2 receptor (NK2R) agonist or a pharmaceutically acceptable salt thereof, wherein the NK2R agonist or the pharmaceutically acceptable salt thereof, has a rapid onset and a short duration of action, to induce one or both of the urinary voiding and defecation. In one embodiment of the presently disclosed subject matter, a method is provided for treating one of urinary voiding and defecation dysfunction in a mammal in need of treatment, which comprises administering on an as-needed basis to the mammal a therapeutically effective amount of [Lys5,MeLeu9,Nle10]-NKA(4-10) (SEQ ID NO: 1), or a pharmaceutically acceptable salt thereof, to induce one or both of the urinary voiding and defecation. Thus, the compositions and methods of the present disclosure meet an existing need for new treatments for urinary voiding and defecation dysfunction including, for example, constipation, the inability to voluntarily defecate, dyssynergia, and flaccid bladder. The urinary voiding and defecation dysfunction can be a result of a wide range of injuries, conditions, diseases, or disorders, including of one or more of spinal cord injury, traumatic brain injury, multiple sclerosis, spina bifida, degenerative brain disease, Alzheimer's, Parkinson's, dementia, diabetes, advanced age, and postoperative status.

In one embodiment of the presently disclosed subject matter, a method is provided for inducing one of urinary voiding and defecation in a mammal, which comprises administering on an as-needed basis to the mammal a therapeutically effective amount of an neurokinin 2 receptor (NK2R) agonist or a pharmaceutically acceptable salt thereof, wherein the NK2R agonist or the pharmaceutically acceptable salt thereof, has a rapid onset and a short duration of action, to induce one or both of the urinary voiding and defecation. In one embodiment of the presently disclosed subject matter, a method is provided for inducing one of urinary voiding and defecation in a mammal, which comprises administering on an as-needed basis to the mammal a therapeutically effective amount of [Lys5,MeLeu9,Nle10]-NKA(4-10) (SEQ ID NO: 1), or a pharmaceutically acceptable salt thereof, to induce one or both of the urinary voiding and defecation. Thus, the compositions and methods of the present disclosure meet an existing need for new treatments to induce urinary voiding and defecation in persons who are, for example, comatose to cause the voiding before the person voids unconsciously. Another advantage of the methods and compostions of the present disclosure is for a pet owner who may want to induce voiding in their normal dog, for example, at a specific, convenient location or time.

In the method for inducing one of urinary voiding and defecation in a mammal, the method may further comprise administering a therapeutically effective amount of a NK2R antagonist, or a pharmaceutically acceptable salt thereof, to terminate at least a majority of the effects of the NK2R agonist, wherein the NK2R antagonist has a duration of action of less than about 4 hours. The NK2R antagonist can have a duration of action of less than about 3 hours. The NK2R antagonist can have a duration of action of less than about 2 hours.

In the method for inducing one of urinary voiding and defecation in a mammal, the NK2R agonist and the NK2R antagonist can be co-administered in either a single or a separate formulation and the onset of action of the NK2R antagonist can be longer than the rapid onset of the NK2R agonist to terminate the majority of the effects of the NK2R agonist within about 10 minutes. The onset of action of the NK2R antagonist can be longer than the rapid onset of the NK2R agonist to terminate the majority of the effects of the NK2R agonist within about 5 minutes.

In the method for inducing one of urinary voiding and defecation in a mammal, the NK2R antagonist can be administered subsequent to administration of the NK2R agonist and after occurrence of the one or both of urinary voiding and defecation, and the onset of action of the NK2R antagonist can range from about 0 to about 10 minutes to terminate the majority of the effects of the NK2R agonist within about 10 minutes. The onset of action of the NK2R antagonist can range from about 0 to about 5 minutes to terminate the majority of the effects of the NK2R agonist within about 5 minutes.

In one embodiment of the presently disclosed subject matter, a method is provided for inducing one of urinary voiding and defecation in a mammal, which comprises: administering on an as-needed basis to the mammal a therapeutically effective amount of a neurokinin 2 receptor (NK2R) agonist or a pharmaceutically acceptable salt thereof, the NK2R agonist having a rapid onset and a short duration of action, to induce the one or both of urinary voiding and defecation; and administering a therapeutically effective amount of a NK2R antagonist, or a pharmaceutically acceptable salt thereof, to terminate at least a majority of the effects of the NK2R agonist after occurance of the one or both of urinary voiding and defecation, wherein the NK2R antagonist has a duration of action of less than about 4 hours. The NK2R antagonist can have a duration of action of less than about 3 hours. The NK2R antagonist can have a duration of action of less than about 2 hours. The NK2R agonist can be [Lys5,MeLeu9,Nle10]-NKA(4-10) (SEQ ID NO: 1), or a pharmaceutically acceptable salt thereof.

The NK2R agonist and the NK2R antagonist can be co-administered and the onset of action of the NK2R antagonist can be longer than the rapid onset of the NK2R agonist to terminate the majority of the effects of the NK2R agonist within about 15 minutes after occurance of the one or both of urinary voiding and defecation. The onset of action of the NK2R antagonist can be longer than the rapid onset of the NK2R agonist to terminate the majority of the effects of the NK2R agonist within about 10 minutes after occurance of the one or both of urinary voiding and defecation. The onset of action of the NK2R antagonist can be longer than the rapid onset of the NK2R agonist to terminate the majority of the effects of the NK2R agonist within about 5 minutes after occurance of the one or both of urinary voiding and defecation.

The NK2R antagonist can be administered subsequent to administration of the NK2R agonist and after the one or both of urinary voiding and defecation, and the onset of action of the NK2R antagonist can range from about 0 to about 15 minutes to terminate the majority of the effects of the NK2R agonist within about 15 minutes of administration. The onset of action of the NK2R antagonist can range from about 0 to about 10 minutes to terminate the majority of the effects of the NK2R agonist within about 10 minutes of administration. The onset of action of the NK2R antagonist can range from about 0 to about 5 minutes to terminate the majority of the effects of the NK2R agonist within about 5 minutes of administration.

It is understood by those of skill in the art that the timing of the administration of the NK2R antagonist in relation to the administration of the NK2R agonist can vary depending on the respective onset and duration of action of each individual NK2R agonist and antagonist chosen to induce voiding and reverse unwanted effects, respectively. The important feature of the timing of the method is that the NK2R antagonist cannot be at effective plasma concentrations during the time when voiding is desired, but must be at effective concentrations during any unwanted effects of the NK2R agonist.

To provide an effective treatment for dyssynergia, the administering of the NK2R agonist according to the methods and formulations of the present disclosure may be combined with one or more urethral relaxants such as, but not limited to, alpha adrenergic receptor blockers, nitric oxide (NO) donors, PDE5 inhibitors, and prostaglandin E receptor (EP1, 2,3) agonists.

A therapeutically effective amount of an active agent of the presently disclosed subject matter may be administered orally, intravenously, subcutaneously, transmucosally (including buccally, sublingually, transurethrally, and rectally), topically, transdermally, by inhalation, intravesically, intrathecally or using any other route of administration.

Methods are provided herein for using an active agent or otherwise referred to herein interchangeably as a "pharmaceutical agent" to provide "on-demand, rapid-onset, short-duration, drug-induced voiding". The drug-induced voiding can be useful for those with voiding dysfunction or for a mammal for which inducing voiding is otherwise desirable. The pharmaceutical agents of the present disclosure can include smooth muscle prokinetics. While there are known pharmaceutical agents that are smooth muscle prokinetics, systemic administration of these agents to a living being can induce death as opposed to therapeutic voiding. In contrast, the compositions and methods of the present disclosure provide pharmaceutical formulations and methods of administration of smooth muscle prokinetic agents to provide a duration of prokinetic action which can produce voiding and then allow the bladder and rectum to subsequently relax to allow for storage of newly-formed urine and stool to prevent subsequent incontinence. The formulations and methods of administration of the present disclosure can minimize the duration of side-effects in other organs systems. The prokinetic agent formulations and methods of administration of the present disclosure can be administered multiple times per day to initiate voiding.

One advantage of the presently described subject matter is provision of smooth muscle prokinetic agents NK2 receptor agonists that have a rapid-onset and short duration of action for administration to mammals to achieve a rapid-onset and short duration contraction of the rectum and bladder. Surprisingly, the contractions produced by administration of these NK2R agonists can actually elicit physiologically significant voiding of stools and urine. In addition, because NK2 receptors are present in the urethra where NK2 receptor stimulation can be expected to cause smooth muscle contraction and closure of the urethra, it was an unexpected finding that these NK2R agonists, administered according to the methods of the present disclosure, can produce contraction of the bladder and voiding of urine. It was similarly unexpected that administration of the NK2R agonists of the present disclosure can produce contraction of the rectum and voiding of stool. For example, stimulation of NK2 receptors in the rectum would have been expected to cause contraction and closure of the anal sphincter and presumably prevention of voiding of stool.

Another advantage of the presently described subject matter is that the NK2R agonist-induced voiding can be achieved without the adverse effect of contractions of the stomach and bowel to produce vomiting and painful cramps.

Another advantage of the presently described subject matter is that the NK2R agonist-induced voiding can be achieved without the adverse effect of contraction of respiratory smooth muscles and difficulty breathing. This is an unexpected advantage, given the presence of NK2 receptors in the respiratory tract, where NK2 receptor stimulation can be expected to cause contraction of the tracheal and bronchial smooth muscle to close the airways.

Another advantage of the presently described subject matter is that methods and composition are provided to reverse any unwanted effects of administration of the NK2R agonist.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

By "LUT" is meant lower urinary tract.

By "GI" is meant gastrointestinal tract.

By "NKA" is meant neuropeptide neurokininA which is a peptide 10 amino acids in length having the sequence His-Lys-Thr-Asp-Ser-Phe-Val-Gly-Leu-Met-NH2 (SEQ ID NO: 2) and which is a peptide agonist for NK2R.

By "NKB" is meant neuropeptide neurokinin B which is a peptide 10 amino acids in length having the sequence Asp-Met-His-Asp-Phe-Phe-Val-Gly-Leu-Met-NH2 (SEQ ID NO: 3).

By "SP" is meant neuropeptide substance P which is a peptide 11 amino acids in length having the sequence Arg-Pro-Lys-Pro-Gln-Gln-Phe-Phe-Gly-Leu-Met-NH2 (SEQ ID NO: 4).

By "NK1R" is meant neurokinin 1 receptor.

By "NK2R" is meant neurokinin 2 receptor.

By "NK3R" is meant neurokinin 3 receptor.

By NKA(4-10) is meant a peptide 7 amino acids in length corresponding to amino acids 4 through 10 of NKA, i.e., Asp4-Ser5-Phe6-Val7-Gly8-Leu9-Met10-NH2 (SEQ ID NO: 5), which is a peptide agonist for NK2R.

By "[Lys5,MeLeu9,Nle10]-NKA(4-10)" (SEQ ID NO: 1) is meant a peptide 7 amino acids in length corresponding to amino acids 4 through 10 of NKA, except that Ser at position 5 of NKA is replaced with Lys, Leu at position 9 is methylated at the nitrogen, and Met at position 10 is replaced with norleucine. "[Lys5,MeLeu9,Nle10]-NKA(4-10)" (SEQ ID NO: 1) is a peptide agonist for NK2R. [Lys5,MeLeu9,Nle10]-NKA(4-10) is in some instances referred to herein as "DTI-100" and the terms "[Lys5,MeLeu9,Nle10]-NKA(4-10)" (SEQ ID NO: 1) and "DTI-100" are used herein interchangeably.

By "[betaAla8]NKA(4-10)" (SEQ ID NO: 6) is meant a peptide 7 amino acids in length corresponding to amino acids 4 through 10 of NKA, except that Ala at position 8 of NKA is a beta amino acid, i.e., Asp-Ser-Phe-Val-β-Ala-Leu-Met-NH2 (SEQ ID NO: 6). [betaAla8]NKA(4-10) (SEQ ID NO: 6) is a peptide agonist for NK2R.

By GR64349 is meant a compound having the structure provided below and which is a peptide agonist for NK2R.

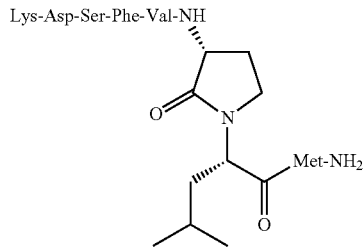

By an "effective" amount or a "therapeutically effective amount" of a drug or pharmacologically active agent of the present disclosure including, for example, a neurokinin 2 receptor (NK2R) agonist, or a pharmaceutically acceptable salt thereof, is meant a nontoxic but sufficient amount of the drug or active agent to provide the desired effect, i.e., treating urinary voiding and/or defecation dysfunction such as effectuating voluntary urinary voiding and/or defecation and/or relieving urinary and/or fecal incontinence. It is recognized that the effective amount of a drug or pharmacologically active agent will vary depending on the route of administration, the selected compound, and the species to which the drug or pharmacologically active agent is administered. It is also recognized that one of skill in the art will determine appropriate effective amounts by taking into account such factors as metabolism, bioavailability, and other factors that affect levels of a drug or pharmacologically active agent following administration within the unit dose ranges disclosed further herein for different routes of administration.

By "pharmaceutically acceptable," such as in the recitation of a "pharmaceutically acceptable carrier," or a "pharmaceutically acceptable acid addition salt," is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. "Pharmacologically active" (or simply "active") as in a "pharmacologically active" derivative or metabolite, refers to a derivative or metabolite having the same type of pharmacological activity as the parent compound. When the term "pharmaceutically acceptable" is used to refer to a derivative (e.g., a salt or an analog) of an active agent, it is to be understood that the compound is pharmacologically active as well, i.e., therapeutically effective for treating urinary voiding and/or defecation dysfunction.

By "continuous" dosing is meant the chronic administration of a selected active agent.

By "as-needed" dosing, also known as "pro re nata" or "prn" dosing, and "on demand" dosing or administration is meant the administration of a single dose of the active agent at some time prior to commencement of emptying of the bladder or bowel. Administration can be immediately prior to such a time, including about 0 minutes, about 0 to about 5 minutes, about 0 to about 10 minutes, about 0 to about 20 minutes, about 0 to about 30 minutes, or about 0 to about 40 minutes, prior to such a time, depending on the formulation and the route of administration.

By "rapid-onset" is intended any period of time up to and including a $T_{max}$ between about 0 sec to about 1 hour, between about 0 sec to about 45 minutes, between about 0 sec to about 30 minutes, between about 0 sec to about 15 minutes, or between about 0 sec to about 10 minutes, or between 0 sec to 5 min, after active agent administration.

By "short duration of action" is intended a $T_{1/2}$ between about 2 hours to about 10 minutes, between about 1 hour to about 10 minutes, and between about 30 minutes to about 10 minutes, and between 15 to about 5 minutes after active agent administration.

The term "delayed release" is used in its conventional sense to refer to a drug formulation that provides for an initial release of the drug after some delay following drug administration and that preferably, although not necessarily, includes a delay of up to about 10 minutes, about 20 minutes, about 30 minutes, about 1 hour, about 2 hours, about 3 hours, about 4 hours, about 5 hours, about 6 hours, about 7 hours, about 8 hours, about 9 hours, about 10 hours, about 11 hours, or about 12 hours.

The term "pulsatile release" is used in its conventional sense to refer to a drug formulation that provides release of the drug in such a way as to produce pulsed plasma profiles of the drug after drug administration.

The term "immediate release" is used in its conventional sense to refer to a drug formulation that provides for release of the drug immediately after drug administration.

By the term "transdermal" drug delivery is meant delivery by passage of a drug through the skin or mucosal tissue and into the bloodstream.

The term "topical administration" is used in its conventional sense to mean delivery of a topical drug or pharmacologically active agent to the skin or mucosa.

The term "oral administration" is used in its conventional sense to mean delivery of a drug through the mouth and ingestion through the stomach and digestive tract.

The term "inhalation administration" is used in its conventional sense to mean delivery of an aerosolized form of the drug by passage through the nose or mouth during inhalation and passage of the drug through the walls of the lungs.

The term "intravesical administration" is used in its conventional sense to mean delivery of a drug directly into the bladder.

The term "intrathecal administration" is used in its conventional sense to mean delivery of a drug directly into the intrathecal space around the spinal cord.

By the term "parenteral" drug delivery is meant delivery by passage of a drug into the blood stream without first having to pass through the alimentary canal, or digestive tract. Parenteral drug delivery may be "subcutaneous," referring to delivery of a drug by administration under the skin. Another form of parenteral drug delivery is "intramuscular," referring to delivery of a drug by administration into muscle tissue. Another form of parenteral drug delivery is "intradermal," referring to delivery of a drug by administration into the skin. An additional form of parenteral drug delivery is "intravenous" or "i.v." or "IV" referring to delivery of a drug by administration into a vein. An additional form of parenteral drug delivery is "intra-arterial," referring to delivery of a drug by administration into an artery. Another form of parenteral drug delivery is "transdermal," referring to delivery of a drug by passage of the drug through the skin and into the bloodstream. Another form of parenteral drug delivery is "intrathecal," referring to delivery of a drug directly into the into the intrathecal space (where fluid flows around the spinal cord).

Still another form of parenteral drug delivery is "transmucosal," referring to administration of a drug to the mucosal surface of an individual so that the drug passes through the mucosal tissue and into the individual's blood stream. Transmucosal drug delivery may be "buccal" or "transbuccal," referring to delivery of a drug by passage through an individual's buccal mucosa and into the bloodstream. Another form of transmucosal drug delivery herein is "lingual" drug delivery, which refers to delivery of a drug by passage of a drug through an individual's lingual mucosa and into the bloodstream. Another form of transmucosal drug delivery herein is "sublingual" drug delivery, which refers to delivery of a drug by passage of a drug through an individual's sublingual mucosa and into the bloodstream. Another form of transmucosal drug delivery is "nasal" or "intranasal" drug delivery, referring to delivery of a drug through an individual's nasal mucosa and into the bloodstream. An additional form of transmucosal drug delivery herein is "rectal" or "transrectal" drug delivery, referring to delivery of a drug by passage of a drug through an individual's rectal mucosa and into the bloodstream. Another form of transmucosal drug delivery is "urethral" or "transurethral" delivery, referring to delivery of the drug into the urethra such that the drug contacts and passes through the wall of the urethra.

The family of endogenous tachykinins is comprised of the neuropeptides substance P (SP), neurokinin A (NKA) and neurokinin B (NKB) (and possibly others). These peptides are naturally occurring in the body and are present in all mammalian species. They are widely distributed in the body, both in the periphery and the central nervous system and are involved in a variety of functions.

The tachykinins SP, NKA and NKB, share a common carboxyl-terminal sequence: Phe-X-Gly-Leu-Met-NH2 (SEQ ID NO: 7), where X is either an aromatic (Tyr or Phe) or a branched aliphatic (Val or Ile) amino acid.

```
NKA:
                                        (SEQ ID NO: 2)
His-Lys-Thr-Asp-Ser-Phe-Val-Gly-Leu-Met-NH2

SP:
                                        (SEQ ID NO: 4)
Arg-Pro-Lys-Pro-Gln-Gln-Phe-Phe-Gly-Leu-Met-NH2

NKB:
                                        (SEQ ID NO: 3)
Asp-Met-His-Asp-Phe-Phe-Val-Gly-Leu-Met-NH2
```

The common carboxyl-terminal sequence, the amidation at the C terminus and the Phe residue at position 5 are essential for biological activity and receptor subtype specificity. All natural tachykinins are amidated at their C terminus; deamidated peptides have been shown to be inactive (Severini, Improta et al. 2002). The minimum chain length required for activity is six residues. The residues from position 7 from the C Terminus have been shown to be important for receptor specificity. Biological activity is greatly reduced if Pro is in position 6. While not wishing to be bound by any particular theory, this effect may be related to Pro affecting the interaction between the C-terminal sequence of the peptide (Phe-Xaa-Gly-Leu-Met-NH2) (SEQ ID NO: 7) and the tachykinin receptors. Pro residue located in positions 8 and 10 may confer affinity and selectivity towards the neurokinin 1 receptor (NK1R).

NKA is a 10 amino-acid peptide. This peptide has been modified in a search for selective and potent NK2R (as well as NK1,3 R) agonists and antagonists (Warner, Miller et al. 2002, Warner, Miller et al. 2003). The following peptides have been used in bladder, GI, and respiratory research as selective and potent agonists for NK2R over NK1R and NK3Rs:

```
[Lys5,MeLeu9,Nle10]-NKA(4-10):
                                        (SEQ ID NO: 1)
Asp-Lys-Phe-Val-Gly-Leu(N-Me)-Nle-NH2

[beta Ala8]NKA(4-10):
                                        (SEQ ID NO: 6)
Asp-Ser-Phe-Val-β-Ala-Leu-Met-NH2

NKA(4-10):
                                        (SEQ ID NO: 5)
Asp4-Ser5-Phe6-Val7-Gly8-Leu9-Met10-NH2
```

There are three tachykinin receptors named neurokinin receptor 1, 2, 3, (NK1R, NK2R and NK3R). The preferred receptor for SP is the NK1Rs, for NKA the NK2Rs and for NKB the NK3Rs. The neurokinin 1, 2, and 3 receptors are 7 transmembrane domain G protein coupled receptors, whose structures have been cloned in several species. Species homology is ~90%. The expression and distribution of tachykinins and NK2 receptors has been investigated in the LUT and GI tract in human tissue and other mammalian tissues (Severini, Improta et al. 2002, Candenas, Lecci et al. 2005, Lecci, Capriati et al. 2006).

In the LUT, the main source of tachykinin peptides (SP and NKA) are the transient receptor potential cation channel subfamily V member 1 (TRPV1) positive afferent neurons (Candenas, Lecci et al. 2005). The peripheral axons of these neurons terminate in the bladder smooth muscle layers and the urothelium (see FIG. 1).

In the GI tract, it has been demonstrated that in addition to afferent nerve fibers, the intrinsic enteric neurons of the myenteric plexus and the intrinsic enteric neurons of the submucosal plexus release tachykinin peptides (Severini, Improta et al. 2002, Lecci, Capriati et al. 2006). In rat and human tissue, NKA immunoreactivity has been found throughout the gastrointestinal tract including the stomach, duodenum, jejunum, ileum and colon (Severini, Improta et al. 2002, Lecci, Capriati et al. 2006). This immunoreactivity has also been shown to be present in ganglia of both the submucosal and myenteric plexuses as well as varicose neurons in the mucosa and the muscle layer of the small and large intestine (Severini, Improta et al. 2002, Lecci, Capriati et al. 2006).

Figure 1:
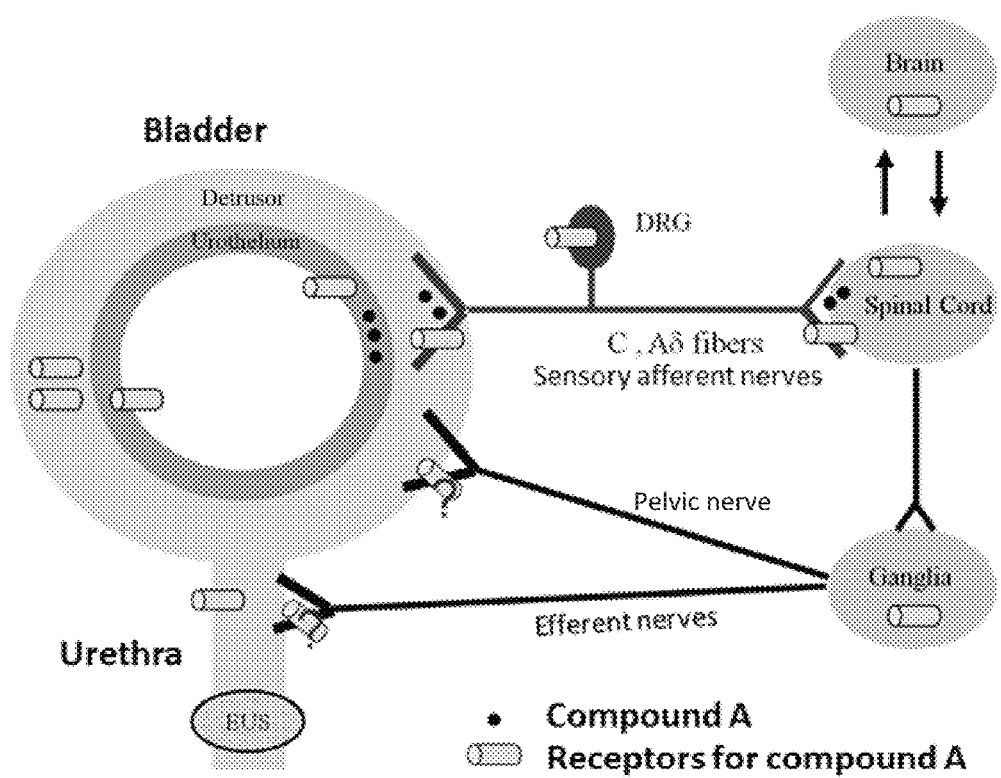
FIG. 1 is a schematic diagram showing sites of action of neurokinin 2 receptors (NK2Rs) in the micturition pathways.
Figure 2:
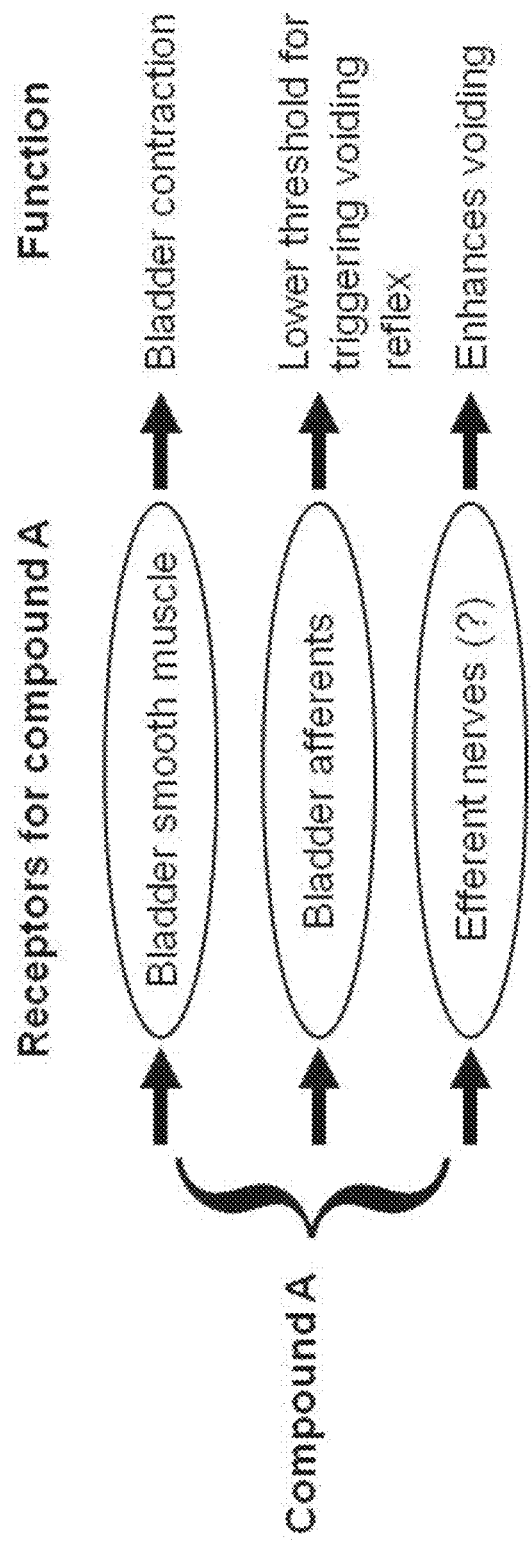
FIG. 2 is a schematic diagram illustrating sites of action and possible effects of NK2R activation in bladder.

In the micturition pathways, NK2Rs may be expressed at many sites (see FIG. 1). These include the smooth muscle of the bladder (multiple species: human (Zeng, Moore et al. 1995; Warner, Miller et al. 2003; Palea, Corsi et al. 1996), hamster (Tramontana, Patacchini et al. 1998) rat, guinea pig, and others (Candenas, Lecci et al. 2005) and primary afferent neurons (Maggi, Santicioli et al. 1986, Maggi, Giuliani et al. 1987). It is not known if these receptors are expressed in bladder efferent neurons.

In one embodiment, the presently disclosed subject matter provides a strategy for administering pharmacological active agents, compositions, and formulations that have distinct pharmacokinetic properties of a rapid-onset of action and a short duration of action, as well as pharmacodynamic properties to contract the bladder and/or colon and induce voiding of urine and/or feces "on demand" when convenient and appropriate for a person suffering from a voiding dysfunction or otherwise in need of such treatment such as, for example, a person who is comatose and may void unconsciously. The compositions and methods of the present disclosure may also be useful to allow a pet owner to induce voiding in their pet at a specific, convenient location or time.

In one embodiment of the present disclosure, a method is provided for treating one or both of urinary voiding and defecation dysfunction in a mammal in need of treatment. In one embodiment of the present disclosure, a method is provided for inducing one or both of urinary voiding and defecation dysfunction in a mammal that may not necessarily have a voiding dysfunction. The methods include administering on an as-needed basis to the mammal a therapeutically effective amount of a neurokinin 2 receptor (NK2R) agonist or a pharmaceutically acceptable salt thereof, wherein the NK2R agonist or the pharmaceutically acceptable salt thereof, has a rapid onset and a short duration of action. The NK2R agonist can include, but is not limited to, Neurokinin A (NKA) (SEQ ID NO: 2), a NKA analogue, including such as, for example, NKA(4-10)) (SEQ ID NO: 5), [Lys5,MeLeu9,Nle10]-NKA(4-10) (SEQ ID NO: 1), [bAla8]NKA(4-10) (SEQ ID NO: 6), and GR 64349. The NK2R agonist can be [Lys5,MeLeu9,Nle10]-NKA(4-10) (SEQ ID NO: 1). The mammal can include but is not limited to, for example, a human, a cat, or a dog. The NK2R agonist or the pharmaceutically acceptable salt thereof, can have selectivity over a neurokinin 1 receptor (NK1R) and a neurokinin 3 receptor (NK3R).

In one embodiment of the present disclosure, a method is provided for inducing one of urinary voiding and defecation in a mammal, which comprises: administering on an as-needed basis to the mammal a therapeutically effective amount of a neurokinin 2 receptor (NK2R) agonist or a pharmaceutically acceptable salt thereof, the NK2R agonist having a rapid onset and a short duration of action, to induce the one or both of urinary voiding and defecation; and administering a therapeutically effective amount of a NK2R antagonist, or a pharmaceutically acceptable salt thereof, to terminate at least a majority of the effects of the NK2R agonist after occurrence of the one or both of urinary voiding and defecation, wherein the NK2R antagonist has a duration of action of less than about 4 hours.

NK2R antagonists of the present disclosure that can be useful to terminate at least a majority of the effects of an administered NK2R agonist can include, but are not limited to: 1) peptide-based tachykinin NK2 receptor antagonists such as, for example, MEN10376, R-396-GR-112,000, PD-147,714, L659,877, MEN11420, and MEN10267 which are described in Quartara et al., *Med Res Rev.* 1995; 15(2): 139-55 (Review); 2) tachykinin NK2 receptor antagonists such as, for example, Nepadutant, Saredutant, Ibodutant (SR 48968), DNK-333, AVE-5833, CS-003, and SSR-241586 which are described in Altamura M, *Expert Opin Ther Pat.* 2012; 22(1):57-77; 3) tachykinin NK2 receptor antagonists such as, for example, GR159897 which is described in Beresford et al., *Eur J Pharmacol.* 1995; 272(2-3):241-8; 4) NK-1/NK-2 receptor antagonists such as, for example, MDL 105,212, which is described in Kudlacz E M et al., *J Pharmacol Exp Ther.* 1996; 279(2):732-9; 5) tachykinin NK2 receptor antagonists such as, for example, MEN15596, which is described in Cialdai C, et al., *Eur J Pharmacol.* 2006; 549(1-3):140-8; 6) NK-2 receptor antagonists such as, for example, GR94800, which is described in McElroy A B, et al., *J Med Chem.* 1992; 35(14):2582-91; and 7) NK-2 receptor antagonists such as, for example, MDL29,913, which is described in Black J L, et al., *Br J Pharmacol.* 1992; 107(2):429-36. The NK2R antagonists of the present disclosure that can be useful to terminate at least a majority of the effects of an administered NK2R agonist can have a duration of action of less than about 4 hours, of less than about 3 hours, or of less than about 2 hours.

Formulations of the compositions and active agents of the present disclosure are provided in as-needed dosage forms, and can include short-term, rapid-onset, rapid-offset, controlled release, delayed release, and pulsatile release formulations, so long as they are formulated to achieve as-needed administration of an active agent, as defined further herein.

In all of the methods and compositions of the present disclosure, the rapid-onset of the NK2R agonist can be characterized by a $T_{max}$ ranging from about 0 sec to about 1 hour after NK2R agonist administration, ranging from about 0 sec to about 45 minutes after NK2R agonist administration, ranging from about 0 sec to about 30 minutes after NK2R agonist administration, ranging from about 0 sec to about 15 minutes after NK2R agonist administration, ranging from about 0 sec to about 10 minutes after NK2R agonist administration, or ranging from about 0 sec to about 5 min after NK2R agonist administration.

In all of the methods and compositions of the present disclosure, the short duration of action of the NK2R agonist can be characterized by a $T_{1/2}$ ranging from about 1 hour to about 10 minutes after NK2R agonist administration, ranging from about 30 minutes to about 10 minutes after NK2R agonist administration, or ranging from about 15 to about 1 minute after NK2R agonist administration.

The NK2R agonist, or the pharmaceutically acceptable salt thereof, can be formulated as an immediate release dosage form and the as-need administering can range from about 0 minutes to about 40 minutes prior to when the voiding and/or defecation is desired, from about 0 minutes to about 20 minutes prior to when the voiding and/or defecation is desired, or from about 0 minutes to about 5 minutes prior to when the voiding and/or defecation is desired. In one embodiment, the NK2R agonist can be [Lys5,MeLeu9,Nle10]-NKA(4-10) (SEQ ID NO: 1).

In one embodiment, one or more additional active agents can be administered either simultaneously or sequentially with the NK2R agonist active agent in either a separate or a single formulation. The additional active agent may be one that is effective in treating bladder and/or bowel dysfunctions that accompany retention, such as overactive bladder or benign prostatic hyperplasia. The additional active agent may be one that potentiates the effect of a NK2R agonist active agent for treating bladder and/or bowel retention. Suitable additional active agents include, but are not limited to, for example, antimuscarinics (e.g. oxybutynin, solifenacin succinate, tolterodine), beta-3 adrenergic agonists (e.g. mirabegron), alpha adrenergic antagonists (e.g. silodosin, terazosin, tamsulosin, doxazosin, prazosin, alfuzosin), 5-alpha reductase inhibitors (e.g. finasteride, dutasteride), phosphodiesterase inhibitors (e.g. sildenafil, vardenafil, tadalafil) and/or any agent that does not inhibit the action of the primary active agent.

The additional active agent may be a urethral relaxant agent such as, for example, an alpha adrenergic receptor blocker, a nitric oxide (NO) donor, a PDE5 inhibitor, or a Prostaglandin E receptor (EP1,2,3) agonist. The alpha adrenergic receptor blocker can be, for example, one of tamsulosin, silodosin, alfuzosin, or naftopidil or any other suitable alpha adrenergic receptor blocker. The NO donor can be, for example, one of sodium nitroprusside, glyceryltrinitrate, or S-nitrosothiol classes of NO donors or any other suitable NO donor. The PDE5 inhibitor can be, for example, one of sildenafil, tadalafil, vardenafil, avanafil, udenafil, dipyridamole, or vardenafil hydrochloride or any other suitable PDE5 inhibitor.

The additional active agent may be a compound that can induce one of colon contraction and/or sphincter relaxation in the subject. The anal sphincter relaxant agent can be, for example, one of vasoactive intestinal polypeptide (VIP), a NO donor, amyl nitrate, butyl nitrate, glyceryltrinitrate, an alpha adrenergic receptor blocker, tamsulosin, silodosin, alfuzosin, or naftopidilor other suitable anal sphincter relaxant agents.

Any of the active agents may be administered in the form of a salt, ester, amide, prodrug, active metabolite, derivative, or the like, provided that the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For example, acid addition salts are prepared from the free base using conventional methodology, and involves reaction with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are salts prepared with organic acids. Conversely, preparation of basic salts of acid moieties which may be present on an active agent are prepared in a similar manner using a pharmaceutically acceptable base such as sodium hydroxide, potassium hydroxide, ammonium hydroxide, calcium hydroxide, trimethylamine, or the like.

Preparation of esters involves functionalization of hydroxyl and/or carboxyl groups that may be present within the molecular structure of the drug. The esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures. Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety, which results in a compound that is therapeutically inactive until modified by an individual's metabolic system.

Other salts, enantiomers, analogs, esters, amides, prodrugs, active metabolites, and derivatives of the active agents may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

The active agents of the present disclosure can be administered by a mode including oral, transmucosal, topical, transdermal, transurethral, transrectal, transnasal, intravesical, intrathecal, implantable, sublingual, inhalation, or parenteral administration.

The active agents of the present disclosure can be contained within a pharmaceutical formulation. The pharmaceutical formulation can be a unit dosage form. The pharmaceutical formulation can be selected from the group consisting of tablets, capsules, caplets, granules, beads, powders, pellets, liquid formulations, solutions, suspensions, syrups, suppositories, creams, ointments, pastes, gels, foams, and sprays.

The pharmaceutical formulation can be a tablet. The pharmaceutical formulation can be a rapidly disintegrating tablet. The tablet can be a rapidly disintegrating open matrix network tablet. The administration can be transmucosal and the rapidly disintegrating open matrix network tablet can include biodegradable polymers or ATRIX BEMA biodegradable polymers. The rapidly disintegrating open matrix network tablet can include biodegradable polymers or ATRIX BEMA biodegradable polymers.

The pharmaceutical formulation can be selected from the group consisting of suppositories, creams, ointments, liquid formulations, pastes, gels, foams, and sprays. The pharmaceutical formulation can be delivered through use of an iontophoresis, an electroporation, or a phonophoresis delivery mechanism. The pharmaceutical formulation can include a permeation enhancer.

The administration of the pharmaceutical formulation can be through a transdermal patch. The transdermal patch can include a permeation enhancer. The transdermal patch can include a needle free transdermal patch comprising electrical energy. The transdermal patch can include a needle free transdermal patch comprising microprojections.

The administration of the pharmaceutical formulation can be parenteral and can include an injection using an injection device.

The administration of the pharmaceutical formulation can be intrathecal and can include use of a programmable infusion pump system.

Suitable compositions and dosage forms include tablets, capsules, caplets, pills, gel caps, troches, dispersions, suspensions, solutions, syrups, transdermal patches, gels, powders, magmas, lozenges, creams, pastes, plasters, lotions, discs, suppositories, liquid sprays for nasal or oral administration, dry powder or aerosolized formulations for inhalation, rapidly disintegrating tablets including effervescent tablets or wafers, ointments, liquid formulations, foams and the like. Further, those of ordinary skill in the art can readily deduce that suitable formulations involving these compositions and dosage forms, including those formulations as described elsewhere herein.

Oral dosage forms include tablets, capsules, caplets, rapidly disintegrating tablets including effervescent tablets or wafers, solutions, suspensions and/or syrups, and may also comprise a plurality of granules, beads, powders or pellets that may or may not be encapsulated. Such dosage forms are prepared using conventional methods known to those in the field of pharmaceutical formulation and described in the pertinent texts, e.g., in Remington: The Science and Practice of Pharmacy, supra. Tablets and capsules represent the most convenient oral dosage forms, in which case solid pharmaceutical carriers are employed.

Tablets may be manufactured using standard tablet processing procedures and equipment. One method for forming tablets is by direct compression of a powdered, crystalline or granular composition containing the active agent(s), alone or in combination with one or more carriers, additives, or the like. As an alternative to direct compression, tablets can be prepared using wet-granulation or dry-granulation processes. Tablets may also be molded rather than compressed, starting with a moist or otherwise tractable material; however, compression and granulation techniques are preferred.

In addition to the active agent(s), tablets prepared for oral administration using the method of the disclosure will generally contain other materials such as binders, diluents, lubricants, disintegrants, fillers, stabilizers, surfactants, preservatives, coloring agents, flavoring agents and the like. Binders are used to impart cohesive qualities to a tablet, and thus ensure that the tablet remains intact after compression. Suitable binder materials include, but are not limited to, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), and Veegum. Diluents are typically necessary to increase bulk so that a practical size tablet is ultimately provided. Suitable diluents include dicalcium phosphate, calcium sulfate, lactose, cellulose, kaolin, mannitol, sodium chloride, dry starch and powdered sugar. Lubricants are used to facilitate tablet manufacture; examples of suitable lubricants include, for example, vegetable oils such as peanut oil, cottonseed oil, sesame oil, olive oil, corn oil, and oil of theobroma, glycerin, magnesium stearate, calcium stearate, and stearic acid. Stearates, if present, preferably represent at no more than approximately 2 wt. % of the drug-containing core. Disintegrants are used to facilitate disintegration of the tablet, and are generally starches, clays, celluloses, algins, gums or crosslinked polymers. Fillers include, for example, materials such as silicon dioxide, titanium dioxide, alumina, talc, kaolin, powdered cellulose and microcrystalline cellulose, as well as soluble materials such as mannitol, urea, sucrose, lactose, dextrose, sodium chloride and sorbitol. Stabilizers are used to inhibit or retard drug decomposition reactions that include, by way of example, oxidative reactions. Surfactants may be anionic, cationic, amphoteric or nonionic surface active agents.

The dosage form may also be a capsule, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. (See, for e.g., Remington: The Science and Practice of Pharmacy, supra), which describes materials and methods for preparing encapsulated pharmaceuticals. If the active agent-containing composition is present within the capsule in liquid form, a liquid carrier is necessary to dissolve the active agent(s). The carrier must be compatible with the capsule material and all components of the pharmaceutical composition, and must be suitable for ingestion.

Solid dosage forms, whether tablets, capsules, caplets, or particulates, may, if desired, be coated so as to provide for delayed release. Dosage forms with delayed release coatings may be manufactured using standard coating procedures and equipment. Such procedures are known to those skilled in the art and described in the pertinent texts (See, for e.g., Remington: The Science and Practice of Pharmacy, supra). Generally, after preparation of the solid dosage form, a delayed release coating composition is applied using a coating pan, an airless spray technique, fluidized bed coating equipment, or the like. Delayed release coating compositions comprise a polymeric material, e.g., cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethylethylcellulose, hydroxypropyl methylcellulose acetate succinate, polymers and copolymers formed from acrylic acid, methacrylic acid, and/or esters thereof.

The dosage form may also be a rapidly disintegrating tablet, including an effervescent tablet or wafer. Effervescent tablets are described in Remington, supra, and examples may be found in the literature, and in, for example, U.S. Pat. No. 5,211,957 to Hagemann et al. Generally, effervescent tablets contain the active agent in combination with additives such as sodium bicarbonate and an organic acid. e.g., tartaric acid or citric acid. In the presence of water, these additives react to liberate carbon dioxide thereby facilitating the disintegration of the tablet. Once the tablet is substantially disintegrated, an individual swallows the resultant solution thereby providing systemic adsorption of the active agent.

Another version of a rapidly disintegrating tablet includes "open matrix network" tablets. These tablets can disintegrate within seconds, i.e., within five to ten seconds, after being placed on the tongue of an individual. The contents of the tablet can then be swallowed with or without water. An example of such a tablet is found in U.S. Pat. No. 4,371,516 to Gregory et al. As described therein, the carrier provides a low density network, e.g., about 10 to about 200 $mg/cm^3$, of water-soluble or water-dispersible material. The tablet is produced by subliming a solution containing both the drug and carrier that is subsequently directed to a mold having tablet-shaped depressions. The carrier may be any suitable material, but is preferably gelatin, with partially hydrolyzed gelatin most preferred. Other examples of rapidly disintegrating tablets that can be adapted to contain active agents as discloses herein are well-known in the art. See, for example, U.S. Pat. No. 5,776,492 to Betzing et al.

Although the present compositions may be administered orally, other modes of administration are suitable as well. For example, transmucosal administration may be advantageously employed. Transmucosal administration is carried out using any type of formulation or dosage unit suitable for application to mucosal tissue. For example, the selected active agent may be administered to the buccal mucosa in an adhesive tablet or patch, sublingually administered by placing a solid dosage form under the tongue, lingually administered by placing a solid dosage form on the tongue, administered nasally as droplets or a nasal spray, administered by inhalation of an aerosol formulation, a non-aerosol liquid formulation, or a dry powder, placed within or near the rectum ("transrectal" formulations), or administered to the urethra as a suppository, ointment, or the like.

Preferred buccal dosage forms will typically comprise a therapeutically effective amount of an active agent and a bioerodible (hydrolyzable) polymeric carrier that may also serve to adhere the dosage form to the buccal mucosa. The buccal dosage unit is fabricated so as to erode over a predetermined time period, wherein drug delivery is provided essentially throughout. The time period can be in the range of from about 0 minutes to about 6 hours. As-needed buccal drug delivery can occur over a time period of from about 0 minutes to about 2 hours, from about 0 minutes to about 1 hour, from about 0 minutes to about 30 minutes, and from about 0 minutes to about 10 minutes. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver.

The "therapeutically effective amount" of the active agent in the buccal dosage unit will of course depend on the potency of the agent and the intended dosage, which, in turn, is dependent on the particular individual undergoing treatment, the specific indication, and the like. The buccal dosage unit will generally contain from about 1.0 wt. % to about 60 wt. % active agent, preferably on the order of from about 1 wt. % to about 30 wt. % active agent. With regard to the bioerodible (hydrolyzable) polymeric carrier, it will be appreciated that virtually any such carrier can be used, so long as the desired drug release profile is not compromised, and the carrier is compatible with the active agent to be administered, and any other components of the buccal dosage unit. Generally, the polymeric carrier comprises a hydrophilic (water-soluble and water-swellable) polymer that adheres to the wet surface of the buccal mucosa. Examples of polymeric carriers useful herein include acrylic acid polymers and co, e.g., those known as "carbomers" (CARBOPOL, which may be obtained from B. F. Goodrich, is one such polymer). Other suitable polymers include, but are not limited to: hydrolyzed polyvinylalcohol; polyethylene oxides (e.g., SENTRY POLYOX water soluble resins, available from Union Carbide); polyacrylates (e.g., GANTREZ, which may be obtained from GAF); vinyl polymers and copolymers; polyvinylpyrrolidone; dextran; guar gum; pectins; starches; and cellulosic polymers such as hydroxypropyl methylcellulose, (e.g., METHOCEL, which may be obtained from the Dow Chemical Company), hydroxypropyl cellulose (e.g., KLUCEL, which may also be obtained from Dow), hydroxypropyl cellulose ethers (see, e.g., U.S. Pat. No. 4,704,285 to Alderman), hydroxyethylcellulose, carboxymethyl cellulose, sodium carboxymethyl cellulose, methyl cellulose, ethyl cellulose, cellulose acetate phthalate, cellulose acetate butyrate, and the like.

Other components may also be incorporated into the buccal dosage forms described herein. The additional components include, but are not limited to, disintegrants, diluents, binders, lubricants, flavoring, colorants, preservatives, and the like. Examples of disintegrants that may be used include, but are not limited to, cross-linked polyvinylpyrrolidones, such as crospovidone (e.g., POLYPLASDONEXL, which may be obtained from GAF), cross-linked carboxylic methylcelluloses, such as croscarmelose (e.g., AC-DI-SOL, which may be obtained from FMC), alginic acid, and sodium carboxymethyl starches (e.g., EXPLOTAB, which may be obtained from Edward Medell Co., Inc.), methylcellulose, agar bentonite and alginic acid. Suitable diluents are those which are generally useful in pharmaceutical formulations prepared using compression techniques, e.g., dicalcium phosphate dihydrate (e.g., DI-TAB, which may be obtained from Stauffer), sugars that have been processed by cocrystallization with dextrin (e.g., co-crystallized sucrose and dextrin such as DI-PAK, which may be obtained from Amstar), calcium phosphate, cellulose, kaolin, mannitol, sodium chloride, dry starch, powdered sugar and the like. Binders, if used, are those that enhance adhesion. Examples of such binders include, but are not limited to, starch, gelatin and sugars such as sucrose, dextrose, molasses, and lactose. Particularly preferred lubricants are stearates and stearic acid, and an optimal lubricant is magnesium stearate.

Sublingual and lingual dosage forms include tablets, creams, ointments, lozenges, pastes, and any other solid dosage form where the active ingredient is admixed into a disintegrable matrix. The tablet, cream, ointment or paste for sublingual or lingual delivery comprises a therapeutically effective amount of the selected active agent and one or more conventional nontoxic carriers suitable for sublingual or lingual drug administration. The sublingual and lingual dosage forms of the present invention can be manufactured using conventional processes. The sublingual and lingual dosage units are fabricated to disintegrate rapidly. The time period for complete disintegration of the dosage unit is typically in the range of from about 10 seconds to about 30 minutes, and optimally is less than 5 minutes.

Other components may also be incorporated into the sublingual and lingual dosage forms described herein. The additional components include, but are not limited to binders, disintegrants, wetting agents, lubricants, and the like. Examples of binders that may be used include water, ethanol, polyvinylpyrrolidone; starch solution gelatin solution, and the like. Suitable disintegrants include dry starch, calcium carbonate, polyoxyethylenesorbitan fatty acid esters, sodium lauryl sulfate, stearic monoglyceride, lactose, and the like. Wetting agents, if used, include glycerin, starches, and the like. Particularly preferred lubricants are stearates and polyethylene glycol. Additional components that may be incorporated into sublingual and lingual dosage forms are known, or will be apparent, to those skilled in this art (See, e.g., Remington: The Science and Practice of Pharmacy, supra).

For transurethral administration, the formulation comprises a urethral dosage form containing the active agent and one or more selected carriers or excipients, such as water, silicone, waxes, petroleum jelly, polyethylene glycol ("PEG"), propylene glycol ("PG"), liposomes, sugars such as mannitol and lactose, and/or a variety of other materials, with polyethylene glycol and derivatives thereof particularly preferred.

Depending on the particular active agent administered, it may be desirable to incorporate a transurethral permeation enhancer in the urethral dosage form. Examples of suitable transurethral permeation enhancers include dimethylsulfoxide ("DMSO"), dimethyl formamide ("DMF"), N,N-dimethylacetamide ("DMA"), decylmethylsulfoxide ("$C_{10}$ MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark AZONE from Nelson Research & Development Co., Irvine, Calif.), SEPA (available from Macrochem Co., Lexington, Mass.), surfactants as discussed above, including, for example, TERGITOL, NONOXYNOL-9 and TWEEN-80, and lower alkanols such as ethanol.

Transurethral drug administration, as explained in U.S. Pat. Nos. 5,242,391, 5,474,535, 5,686,093 and 5,773,020, can be carried out in a number of different ways using a variety of urethral dosage forms. For example, the drug can be introduced into the urethra from a flexible tube, squeeze bottle, pump or aerosol spray. The drug may also be contained in coatings, pellets or suppositories that are absorbed, melted or bioeroded in the urethra. In certain embodiments, the drug is included in a coating on the exterior surface of a penile insert. It is preferred, although not essential, that the drug be delivered from at least about 3 cm into the urethra, and preferably from at least about 7 cm into the urethra. Generally, delivery from at least about 3 cm to about 8 cm into the urethra will provide effective results in conjunction with the present method.

Urethral suppository formulations containing PEG or a PEG derivative may be conveniently formulated using conventional techniques, e.g., compression molding, heat molding or the like, as will be appreciated by those skilled in the art and as described in the pertinent literature and pharmaceutical texts. (See, e.g., Remington: The Science and Practice of Pharmacy, supra), which discloses typical methods of preparing pharmaceutical compositions in the form of urethral suppositories. The PEG or PEG derivative preferably has a molecular weight in the range of from about 200 to about 2,500 g/mol, more preferably in the range of from about 1,000 to about 2,000 g/mol. Suitable polyethylene glycol derivatives include polyethylene glycol fatty acid esters, for example, polyethylene glycol monostearate, polyethylene glycol sorbitan esters, e.g., polysorbates, and the like. Depending on the particular active agent, it may also be preferred that urethral suppositories contain one or more solubilizing agents effective to increase the solubility of the active agent in the PEG or other transurethral vehicle.

It may be desirable to deliver the active agent in a urethral dosage form that provides for controlled release of the agent. In such a case, the dosage form comprises a biocompatible, biodegradable material, typically a biodegradable polymer. Examples of such polymers include polyesters, polyalkylcyanoacrylates, polyorthoesters, polyanhydrides, albumin, gelatin and starch. As explained, for example, in PCT Publication No. WO 96/40054, these and other polymers can be used to provide biodegradable microparticles that enable controlled drug release.

The urethral dosage form will preferably comprise a suppository that is on the order of from about 2 to about 20 mm in length, preferably from about 5 to about 10 mm in length, and less than about 5 mm in width, preferably less than about 2 mm in width. The weight of the suppository will typically be in the range of from about 1 mg to about 100 mg, preferably in the range of from about 1 mg to about 50 mg. However, it will be appreciated by those skilled in the art that the size of the suppository can and will vary, depending on the potency of the drug, the nature of the formulation, and other factors.

Transurethral drug delivery may involve an "active" delivery mechanism such as iontophoresis, electroporation or phonophoresis. Devices and methods for delivering drugs in this way are well known in the art. Iontophoretically assisted drug delivery is, for example, described in PCT Publication No. WO 96/40054, cited above. Briefly, the active agent is driven through the urethral wall by means of an electric current passed from an external electrode to a second electrode contained within or affixed to a urethral probe.

Preferred transrectal dosage forms include rectal suppositories, creams, ointments, and liquid formulations (enemas). The suppository, cream, ointment or liquid formulation for transrectal delivery comprises a therapeutically effective amount of the selected active ingredient and one or more conventional nontoxic carriers suitable for transrectal drug administration. The transrectal dosage forms of the present invention can be manufactured using conventional processes. The transrectal dosage unit can be fabricated to disintegrate rapidly or over a period of several hours. The time period for complete disintegration is preferably in the range of from about 1 minute to about 6 hours, and optimally is less than about 3 hours.

Other components may also be incorporated into the transrectal dosage forms described herein. The additional components include, but are not limited to, stiffening agents, antioxidants, preservatives, and the like. Examples of stiffening agents that may be used include, for example, paraffin, white wax and yellow wax. Preferred antioxidants, if used, include sodium bisulfite and sodium metabisulfite.

The active agents may also be administered intranasally or by inhalation. Compositions for intranasal administration are generally liquid formulations for administration as a spray or in the form of drops, although powder formulations for intranasal administration, e.g., insufflations, are also known, as are nasal gels, creams, pastes or ointments. For liquid formulations, the active agent can be formulated into a solution, e.g., water or isotonic saline, buffered or unbuffered, or as a suspension. Preferably, such solutions or suspensions are isotonic relative to nasal secretions and of about the same pH, ranging e.g., from about pH 4.0 to about pH 7.4 or, from about pH 6.0 to about pH 7.0. Buffers should be physiologically compatible and include, simply by way of example, phosphate buffers. Furthermore, various devices are available in the art for the generation of drops, droplets and sprays, including droppers, squeeze bottles, and manually and electrically powered intranasal pump dispensers. Active agent containing intranasal carriers may also include nasal gels, creams, pastes or ointments with a viscosity of, e.g., from about 10 to about 6500 cps, or greater, depending on the desired sustained contact with the nasal mucosal surfaces. Such carrier viscous formulations may be based upon, simply by way of example, alkylcelluloses and/or other biocompatible carriers of high viscosity well known to the art (see e.g., Remington: The Science and Practice of Pharmacy, supra). Other ingredients, such as art known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. Formulations for inhalation may be prepared as an aerosol, either a solution aerosol in which the active agent is solubilized in a carrier (e.g., propellant) or a dispersion aerosol in which the active agent is suspended or dispersed throughout a carrier and an optional solvent. Non-aerosol formulations for inhalation may take the form of a liquid, typically an aqueous suspension, although aqueous solutions may be used as well. In such a case, the carrier is typically a sodium chloride solution having a concentration such that the formulation is isotonic relative to normal body fluid. In addition to the carrier, the liquid formulations may contain water and/or excipients including an antimicrobial preservative (e.g., benzalkonium chloride, benzethonium chloride, chlorobutanol, phenylethyl alcohol, thimerosal and combinations thereof), a buffering agent (e.g., citric acid, potassium metaphosphate, potassium phosphate, sodium acetate, sodium citrate, and combinations thereof), a surfactant (e.g., polysorbate 80, sodium lauryl sulfate, sorbitanmonopalmitate and combinations thereof), and/or a suspending agent (e.g., agar, bentonite, microcrystalline cellulose, sodium carboxymethylcellulose, hydroxypropyl methylcellulose, tragacanth, veegum and combinations thereof). Non-aerosol formulations for inhalation may also comprise dry powder formulations, particularly insufflations in which the powder has an average particle size of from about 0.1 μm to about 50 μm, from about 1 μm to about 25 μm.

Topical formulations may be in any form suitable for application to the body surface, and may comprise, for example, an ointment, cream, gel, lotion, solution, paste or the like, and/or may be prepared so as to contain liposomes, micelles, and/or microspheres. Preferred topical formulations herein are ointments, creams and gels.

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington: The Science and Practice of Pharmacy, supra, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glycerylmonostearate, lanolin and stearic acid. Preferred water-soluble ointment bases are prepared from polyethylene glycols of varying molecular weight (See, e.g., Remington: The Science and Practice of Pharmacy, supra).

Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are cross-linked acrylic acid polymers such as the "carbomer" family of polymers, e.g., carboxypolyalkylenes that may be obtained commercially under the CARBOPOL trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

Various additives, known to those skilled in the art, may be included in the topical formulations. For example, solubilizers may be used to solubilize certain active agents. For those drugs having an unusually low rate of permeation through the skin or mucosal tissue, it may be desirable to include a permeation enhancer in the formulation; suitable enhancers are as described elsewhere herein.

The compounds of the invention may also be administered through the skin or mucosal tissue using conventional transdermal drug delivery systems, wherein the agent is contained within a laminated structure (typically referred to as a transdermal "patch") that serves as a drug delivery device to be affixed to the skin. Transdermal drug delivery may involve passive diffusion or it may be facilitated using electrotransport, e.g., iontophoresis. In a typical transdermal "patch," the drug composition is contained in a layer, or "reservoir," underlying an upper backing layer. The laminated structure may contain a single reservoir, or it may contain multiple reservoirs. In one type of patch, referred to as a "monolithic" system, the reservoir is comprised of a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active agent and any other materials that are present, the backing is preferably made of a sheet or film of a flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the basal surface thereof, either the drug reservoir or a separate contact adhesive layer, so that the system may be affixed to the skin. The release liner should be made from a drug/vehicle impermeable material.

Transdermal drug delivery systems may in addition contain a skin permeation enhancer. That is, because the inherent permeability of the skin to some drugs may be too low to allow therapeutic levels of the drug to pass through a reasonably sized area of unbroken skin, it is necessary to coadminister a skin permeation enhancer with such drugs. Suitable enhancers are well known in the art and include, for example, those enhancers listed above in transmucosal compositions.

In one embodiment of the present disclosure, the active agent is administered transdermally. The transdermal administration can include use of a transdermal patch. The transdermal patch can include a permeation enhancer. The transdermal patch can include a needle free transdermal patch that includes use of electrical energy. The needle free transdermal patch that includes use of electrical energy can be VYTERIS SMART PATCH DRUG DELIVERY. The transdermal patch can include a needle free transdermal patch having microprojections. The needle free transdermal patch having microprojections can be ZP PATCH TECHNOLOGY. The needle free transdermal patch can be a V-GO patch.

Parenteral administration, if used, is generally characterized by injection, including intramuscular, intraperitoneal, intravenous (i.v.) and subcutaneous injection. Injectable formulations can be prepared in conventional forms, either as liquid solutions or suspensions; solid forms suitable for solution or suspension in liquid prior to injection, or as emulsions. Preferably, sterile injectable suspensions are formulated according to techniques known in the art using suitable dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium.

Intravesical administration, if used, is generally characterized by administration directly into the bladder and may include methods as described elsewhere herein. Other methods of intravesical administration may include those described in U.S. Pat. Nos. 6,207,180 and 6,039,967, as well as other methods that are known to one of skill in the art.

Intrathecal administration, if used, is generally characterized by administration directly into the intrathecal space (where fluid flows around the spinal cord).

One common system utilized for intrathecal administration is the fully implantable, programmable SYNCHROMED II PROGRAMMABLE INFUSION PUMP SYSTEM. The SYNCHROMED II PROGRAMMABLE INFUSION PUMP SYSTEM has two parts that are both placed in the body during a surgical procedure: the catheter and the pump. The catheter is a small, soft tube. One end is connected to the catheter port of the pump, and the other end is placed in the intrathecal space. The pump is a round metal device about one inch (2.5 cm) thick, three inches (8.5 cm) in diameter, and weighs about six ounces (205 g) that stores and releases prescribed amounts of medication directly into the intrathecal space. It is made of titanium, a lightweight, medical-grade metal. The reservoir is the space inside the pump that holds the medication. The fill port is a raised center portion of the pump through which the pump is refilled. The doctor or a nurse inserts a needle through the patient's skin and through the fill port to fill the pump. Some pumps have a side catheter access port that allows the doctor to inject other medications or sterile solutions directly into the catheter, bypassing the pump.

The SYNCHROMED II PROGRAMMABLE INFUSION PUMP automatically delivers a controlled amount of medication through the catheter to the intrathecal space around the spinal cord, where it is most effective. The exact dosage, rate and timing prescribed by the doctor are entered in the pump using a programmer, an external computer-like device that controls the pump's memory. Information about the patient's prescription is stored in the pump's memory. The doctor can easily review this information by using the programmer. The programmer communicates with the pump by radio signals that allow the doctor to tell how the pump is operating at any given time. The doctor also can use the programmer to change your medication dosage.

Flowonix has developed an implantable, programmable drug pump (PROMETRA) designed to deliver therapeutic drugs into the spine to relieve a variety of chronic disorders and help patients return to normal lives.

Methods of intrathecal administration may include those described above, as well as other methods that are known to one of skill in the art.

Other controlled release systems include those developed by ALZA Corporation based upon: 1) osmotic technology for oral delivery; 2) transdermal delivery via patches; 3) liposomal delivery via intravenous injection; 4) osmotic technology for long-term delivery via implants; and 5) depot technology designed to deliver agents for periods of days to a month. ALZA oral delivery systems include those that employ osmosis to provide precise, controlled drug delivery for up to 24 hours for both poorly soluble and highly soluble drugs, as well as those that deliver high drug doses meeting high drug loading requirements. ALZA liposomal delivery systems involve lipid nanoparticles that evade recognition by the immune system because of their unique polyethylene glycol (PEG) coating, allowing the precise delivery of drugs to disease-specific areas of the body. ALZA also has developed osmotically driven systems to enable the continuous delivery of small drugs, peptides, proteins, DNA and other bioactive macromolecules for up to one year for systemic or tissue-specific therapy. Finally, ALZA depot injection therapy is designed to deliver biopharmaceutical agents and small molecules for periods of days to a month using a nonaqueous polymer solution for the stabilization of macromolecules and a unique delivery profile.

Examples of controlled release formulations, tablets, dosage forms, and drug delivery systems that are suitable for use with the present disclosure are described in the following US patents assigned to ALZA Corporation: U.S. Pat. No. 4,367,741; U.S. Pat. No. 4,402,695; U.S. Pat. No. 4,418,038; U.S. Pat. No. 4,434,153; U.S. Pat. No. 4,439,199; U.S. Pat. No. 4,450,198; U.S. Pat. No. 4,455,142; U.S. Pat. No. 4,455,144; U.S. Pat. No. 4,484,923; U.S. Pat. No. 4,486,193; U.S. Pat. No. 4,489,197; U.S. Pat. No. 4,511,353; U.S. Pat. No. 4,519,801; U.S. Pat. No. 4,526,578; U.S. Pat. No. 4,526,933; U.S. Pat. No. 4,534,757; U.S. Pat. No. 4,553,973; U.S. Pat. No. 4,559,222; U.S. Pat. No. 4,564,364; U.S. Pat. No. 4,578,075; U.S. Pat. No. 4,588,580; U.S. Pat. No. 4,610,686; U.S. Pat. No. 4,618,487; U.S. Pat. No. 4,627,851; U.S. Pat. No. 4,629,449; U.S. Pat. No. 4,642,233; U.S. Pat. No. 4,649,043; U.S. Pat. No. 4,650,484; U.S. Pat. No. 4,659,558; U.S. Pat. No. 4,661,105; U.S. Pat. No. 4,662,880; U.S. Pat. No. 4,675,174; U.S. Pat. No. 4,681,583; U.S. Pat. No. 4,684,524; U.S. Pat. No. 4,692,336; U.S. Pat. No.

4,693,895; U.S. Pat. No. 4,704,119; U.S. Pat. No. 4,705,515; U.S. Pat. No. 4,717,566; U.S. Pat. No. 4,721,613; U.S. Pat. No. 4,723,957; U.S. Pat. No. 4,725,272; U.S. Pat. No. 4,728,498; U.S. Pat. No. 4,743,248; U.S. Pat. No. 4,747,847; U.S. Pat. No. 4,751,071; U.S. Pat. No. 4,753,802; U.S. Pat. No. 4,755,180; U.S. Pat. No. 4,756,314; U.S. Pat. No. 4,764,380; U.S. Pat. No. 4,773,907; U.S. Pat. No. 4,777,049; U.S. Pat. No. 4,781,924; U.S. Pat. No. 4,786,503; U.S. Pat. No. 4,788,062; U.S. Pat. No. 4,810,502; U.S. Pat. No. 4,812,313; U.S. Pat. No. 4,816,258; U.S. Pat. No. 4,824,675; U.S. Pat. No. 4,834,979; U.S. Pat. No. 4,837,027; U.S. Pat. No. 4,842,867; U.S. Pat. No. 4,846,826; U.S. Pat. No. 4,847,093; U.S. Pat. No. 4,849,226; U.S. Pat. No. 4,851,229; U.S. Pat. No. 4,851,231; U.S. Pat. No. 4,851,232; U.S. Pat. No. 4,853,229; U.S. Pat. No. 4,857,330; U.S. Pat. No. 4,859,470; U.S. Pat. No. 4,863,456; U.S. Pat. No. 4,863,744; U.S. Pat. No. 4,865,598; U.S. Pat. No. 4,867,969; U.S. Pat. No. 4,871,548; U.S. Pat. No. 4,872,873; U.S. Pat. No. 4,874,388; U.S. Pat. No. 4,876,093; U.S. Pat. No. 4,892,778; U.S. Pat. No. 4,902,514; U.S. Pat. No. 4,904,474; U.S. Pat. No. 4,913,903; U.S. Pat. No. 4,915,949; U.S. Pat. No. 4,915,952; U.S. Pat. No. 4,917,895; U.S. Pat. No. 4,931,285; U.S. Pat. No. 4,946,685; U.S. Pat. No. 4,948,592; U.S. Pat. No. 4,954,344; U.S. Pat. No. 4,957,494; U.S. Pat. No. 4,960,416; U.S. Pat. No. 4,961,931; U.S. Pat. No. 4,961,932; U.S. Pat. No. 4,963,141; U.S. Pat. No. 4,966,769; U.S. Pat. No. 4,971,790; U.S. Pat. No. 4,976,966; U.S. Pat. No. 4,986,987; U.S. Pat. No. 5,006,346; U.S. Pat. No. 5,017,381; U.S. Pat. No. 5,019,397; U.S. Pat. No. 5,023,076; U.S. Pat. No. 5,023,088; U.S. Pat. No. 5,024,842; U.S. Pat. No. 5,028,434; U.S. Pat. No. 5,030,454; U.S. Pat. No. 5,071,656; U.S. Pat. No. 5,077,054; U.S. Pat. No. 5,082,668; U.S. Pat. No. 5,104,390; U.S. Pat. No. 5,110,597; U.S. Pat. No. 5,122,128; U.S. Pat. No. 5,125,894; U.S. Pat. No. 5,141,750; U.S. Pat. No. 5,141,752; U.S. Pat. No. 5,156,850; U.S. Pat. No. 5,160,743; U.S. Pat. No. 5,160,744; U.S. Pat. No. 5,169,382; U.S. Pat. No. 5,171,576; U.S. Pat. No. 5,176,665; U.S. Pat. No. 5,185,158; U.S. Pat. No. 5,190,765; U.S. Pat. No. 5,198,223; U.S. Pat. No. 5,198,229; U.S. Pat. No. 5,200,195; U.S. Pat. No. 5,200,196; U.S. Pat. No. 5,204,116; U.S. Pat. No. 5,208,037; U.S. Pat. No. 5,209,746; U.S. Pat. No. 5,221,254; U.S. Pat. No. 5,221,278; U.S. Pat. No. 5,229,133; U.S. Pat. No. 5,232,438; U.S. Pat. No. 5,232,705; U.S. Pat. No. 5,236,689; U.S. Pat. No. 5,236,714; U.S. Pat. No. 5,240,713; U.S. Pat. No. 5,246,710; U.S. Pat. No. 5,246,711; U.S. Pat. No. 5,252,338; U.S. Pat. No. 5,254,349; U.S. Pat. No. 5,266,332; U.S. Pat. No. 5,273,752; U.S. Pat. No. 5,284,660; U.S. Pat. No. 5,286,491; U.S. Pat. No. 5,308,348; U.S. Pat. No. 5,318,558; U.S. Pat. No. 5,320,850; U.S. Pat. No. 5,322,502; U.S. Pat. No. 5,326,571; U.S. Pat. No. 5,330,762; U.S. Pat. No. 5,338,550; U.S. Pat. No. 5,340,590; U.S. Pat. No. 5,342,623; U.S. Pat. No. 5,344,656; U.S. Pat. No. 5,348,746; U.S. Pat. No. 5,358,721; U.S. Pat. No. 5,364,630; U.S. Pat. No. 5,376,377; U.S. Pat. No. 5,391,381; U.S. Pat. No. 5,402,777; U.S. Pat. No. 5,403,275; U.S. Pat. No. 5,411,740; U.S. Pat. No. 5,417,675; U.S. Pat. No. 5,417,676; U.S. Pat. No. 5,417,682; U.S. Pat. No. 5,423,739; U.S. Pat. No. 5,424,289; U.S. Pat. No. 5,431,919; U.S. Pat. No. 5,443,442; U.S. Pat. No. 5,443,459; U.S. Pat. No. 5,443,461; U.S. Pat. No. 5,456,679; U.S. Pat. No. 5,460,826; U.S. Pat. No. 5,462,741; U.S. Pat. No. 5,462,745; U.S. Pat. No. 5,489,281; U.S. Pat. No. 5,499,979; U.S. Pat. No. 5,500,222; U.S. Pat. No. 5,512,293; U.S. Pat. No. 5,512,299; U.S. Pat. No. 5,529,787; U.S. Pat. No. 5,531,736; U.S. Pat. No. 5,532,003; U.S. Pat. No. 5,533,971; U.S. Pat. No. 5,534,263; U.S. Pat. No. 5,540,912; U.S. Pat. No. 5,543,156; U.S. Pat. No. 5,571,525; U.S. Pat. No. 5,573,503; U.S. Pat. No. 5,591,124; U.S. Pat. No. 5,593,695; U.S. Pat. No. 5,595,759; U.S. Pat. No. 5,603,954; U.S. Pat. No. 5,607,696; U.S. Pat. No. 5,609,885; U.S. Pat. No. 5,614,211; U.S. Pat. No. 5,614,578; U.S. Pat. No. 5,620,705; U.S. Pat. No. 5,620,708; U.S. Pat. No. 5,622,530; U.S. Pat. No. 5,622,944; U.S. Pat. No. 5,633,011; U.S. Pat. No. 5,639,477; U.S. Pat. No. 5,660,861; U.S. Pat. No. 5,667,804; U.S. Pat. No. 5,667,805; U.S. Pat. No. 5,674,895; U.S. Pat. No. 5,688,518; U.S. Pat. No. 5,698,224; U.S. Pat. No. 5,702,725; U.S. Pat. No. 5,702,727; U.S. Pat. No. 5,707,663; U.S. Pat. No. 5,713,852; U.S. Pat. No. 5,718,700; U.S. Pat. No. 5,736,580; U.S. Pat. No. 5,770,227; U.S. Pat. No. 5,780,058; U.S. Pat. No. 5,783,213; U.S. Pat. No. 5,785,994; U.S. Pat. No. 5,795,591; U.S. Pat. No. 5,811,465; U.S. Pat. No. 5,817,624; U.S. Pat. No. 5,824,340; U.S. Pat. No. 5,830,501; U.S. Pat. No. 5,830,502; U.S. Pat. No. 5,840,754; U.S. Pat. No. 5,858,407; U.S. Pat. No. 5,861,439; U.S. Pat. No. 5,863,558; U.S. Pat. No. 5,876,750; U.S. Pat. No. 5,883,135; U.S. Pat. No. 5,897,878; U.S. Pat. No. 5,904,934; U.S. Pat. No. 5,904,935; U.S. Pat. No. 5,906,832; U.S. Pat. No. 5,912,268; U.S. Pat. No. 5,914,131; U.S. Pat. No. 5,916,582; U.S. Pat. No. 5,932,547; U.S. Pat. No. 5,938,654; U.S. Pat. No. 5,941,844; U.S. Pat. No. 5,955,103; U.S. Pat. No. 5,972,369; U.S. Pat. No. 5,972,370; U.S. Pat. No. 5,972,379; U.S. Pat. No. 5,980,943; U.S. Pat. No. 5,981,489; U.S. Pat. No. 5,983,130; U.S. Pat. No. 5,989,590; U.S. Pat. No. 5,995,869; U.S. Pat. No. 5,997,902; U.S. Pat. No. 6,001,390; U.S. Pat. No. 6,004,309; U.S. Pat. No. 6,004,578; U.S. Pat. No. 6,008,187; U.S. Pat. No. 6,020,000; U.S. Pat. No. 6,034,101; U.S. Pat. No. 6,036,973; U.S. Pat. No. 6,039,977; U.S. Pat. No. 6,057,374; U.S. Pat. No. 6,066,619; U.S. Pat. No. 6,068,850; U.S. Pat. No. 6,077,538; U.S. Pat. No. 6,083,190; U.S. Pat. No. 6,096,339; U.S. Pat. No. 6,106,845; U.S. Pat. No. 6,110,499; U.S. Pat. No. 6,120,798; U.S. Pat. No. 6,120,803; U.S. Pat. No. 6,124,261; U.S. Pat. No. 6,130,200; U.S. Pat. No. 6,146,662; U.S. Pat. No. 6,153,678; U.S. Pat. No. 6,174,547; U.S. Pat. No. 6,183,466; U.S. Pat. No. 6,203,817; U.S. Pat. No. 6,210,712; U.S. Pat. No. 6,210,713; U.S. Pat. No. 6,224,907; U.S. Pat. No. 6,235,712; U.S. Pat. No. 6,245,357; U.S. Pat. No. 6,262,115; U.S. Pat. No. 6,264,990; U.S. Pat. No. 6,267,984; U.S. Pat. No. 6,287,598; U.S. Pat. No. 6,289,241; U.S. Pat. No. 6,331,311; U.S. Pat. No. 6,333,050; U.S. Pat. No. 6,342,249; U.S. Pat. No. 6,346,270; U.S. Pat. No. 6,365,183; U.S. Pat. No. 6,368,626; U.S. Pat. No. 6,387,403; U.S. Pat. No. 6,419,952; U.S. Pat. No. 6,440,457; U.S. Pat. No. 6,468,961; U.S. Pat. No. 6,491,683; U.S. Pat. No. 6,512,010; U.S. Pat. No. 6,514,530; U.S. Pat. No. 6,534,089; U.S. Pat. No. 6,544,252; U.S. Pat. No. 6,548,083; U.S. Pat. No. 6,551,613; U.S. Pat. No. 6,572,879; and U.S. Pat. No. 6,596,314.

Other examples of controlled release formulations, tablets, dosage forms, and drug delivery systems that are suitable for use with the present invention are described in the following published U.S. patent application and PCT applications assigned to ALZA Corporation: US20010051183; WO0004886; WO0013663; WO0013674; WO0025753; WO0025790; WO0035419; WO0038650; WO0040218; WO0045790; WO0066126; WO0074650; WO0119337; WO0119352; WO0121211; WO0137815; WO0141742; WO0143721; WO0156543; WO03041684; WO03041685; WO03041757; WO03045352; WO03051341; WO03053400; WO03053401; WO9000416; WO9004965; WO9113613; WO9116884; WO9204011; WO9211843; WO9212692; WO9213521; WO9217239; WO9218102; WO9300071; WO9305843; WO9306819; WO9314813; WO9319739; WO9320127; WO9320134; WO9407562; WO9408572; WO9416699; WO9421262;

WO9427587; WO9427589; WO9503823; WO9519174; WO9529665; WO9600065; WO9613248; WO9625922; WO9637202; WO9640049; WO9640050; WO9640139; WO9640364; WO9640365; WO9703634; WO9800158; WO9802169; WO9814168; WO9816250; WO9817315; WO9827962; WO9827963; WO9843611; WO9907342; WO9912526; WO9912527; WO9918159; WO9929297; WO9929348; WO9932096; WO9932153; WO9948494; WO9956730; WO9958115; and WO9962496.

Andrx Corporation has also developed drug delivery technology suitable for use in the presently disclosed subject matter that includes: 1) a pelletized pulsatile delivery system ("PPDS"); 2) a single composition osmotic tablet system ("SCOT"); 3) a solubility modulating hydrogel system ("SMHS"); 4) a delayed pulsatile hydrogel system ("DPHS"); 5) a stabilized pellet delivery system ("SPDS"); 6) a granulated modulating hydrogel system ("GMHS"); 7) a pelletized tablet system ("PELTAB"); 8) a porous tablet system ("PORTAB"); and 9) a stabilized tablet delivery system ("STDS"). PPDS uses pellets that are coated with specific polymers and agents to control the release rate of the microencapsulated drug and is designed for use with drugs that require a pulsed release. SCOT utilizes various osmotic modulating agents as well as polymer coatings to provide a zero-order drug release. SMHS utilizes a hydrogel-based dosage system that avoids the "initial burst effect" commonly observed with other sustained-release hydrogel formulations and that provides for sustained release without the need to use special coatings or structures that add to the cost of manufacturing. DPHS is designed for use with hydrogel matrix products characterized by an initial zero-order drug release followed by a rapid release that is achieved by the blending of selected hydrogel polymers to achieve a delayed pulse. SPDS incorporates a pellet core of drug and protective polymer outer layer, and is designed specifically for unstable drugs, while GMHS incorporates hydrogel and binding polymers with the drug and forms granules that are pressed into tablet form. PELTAB provides controlled release by using a water insoluble polymer to coat discrete drug crystals or pellets to enable them to resist the action of fluids in the gastrointestinal tract, and these coated pellets are then compressed into tablets. PORTAB provides controlled release by incorporating an osmotic core with a continuous polymer coating and a water soluble component that expands the core and creates microporous channels through which drug is released. Finally, STDS includes a dual layer coating technique that avoids the need to use a coating layer to separate the enteric coating layer from the omeprazole core.

Examples of controlled release formulations, tablets, dosage forms, and drug delivery systems that are suitable for use with the present invention are described in the following US patents assigned to Andrx Corporation: U.S. Pat. No. 5,397,574; U.S. Pat. No. 5,419,917; U.S. Pat. No. 5,458,887; U.S. Pat. No. 5,458,888; U.S. Pat. No. 5,472,708; U.S. Pat. No. 5,508,040; U.S. Pat. No. 5,558,879; U.S. Pat. No. 5,567,441; U.S. Pat. No. 5,654,005; U.S. Pat. No. 5,728,402; U.S. Pat. No. 5,736,159; U.S. Pat. No. 5,830,503; U.S. Pat. No. 5,834,023; U.S. Pat. No. 5,837,379; U.S. Pat. No. 5,916,595; U.S. Pat. No. 5,922,352; U.S. Pat. No. 6,099,859; U.S. Pat. No. 6,099,862; U.S. Pat. No. 6,103,263; U.S. Pat. No. 6,106,862; U.S. Pat. No. 6,156,342; U.S. Pat. No. 6,177,102; U.S. Pat. No. 6,197,347; U.S. Pat. No. 6,210,716; U.S. Pat. No. 6,238,703; U.S. Pat. No. 6,270,805; U.S. Pat. No. 6,284,275; U.S. Pat. No. 6,485,748; U.S. Pat. No. 6,495,162; U.S. Pat. No. 6,524,620; U.S. Pat. No. 6,544,556; U.S. Pat. No. 6,589,553; U.S. Pat. No. 6,602,522; and U.S. Pat. No. 6,610,326.

Examples of controlled release formulations, tablets, dosage forms, and drug delivery systems that are suitable for use with the present disclosure are described in the following published US and PCT patent applications assigned to Andrx Corporation: US20010024659; US 20020115718; US 20020156066; WO0004883; WO0009091; WO0012097; WO0027370; WO0050010; WO0132161; WO0134123; WO0236077; WO0236100; WO02062299; WO02062824; WO02065991; WO02069888; WO02074285; WO03000177; WO9521607; WO9629992; WO9633700; WO9640080; WO9748386; WO9833488; WO9833489; WO9930692; WO9947125; and WO9961005.

Some other examples of drug delivery approaches focus on non-oral drug delivery, providing parenteral, transmucosal, and topical delivery of proteins, peptides, and small molecules. For example, the ATRIGEL drug delivery system developed by Atrix Laboratories Inc. comprises biodegradable polymers, similar to those used in biodegradable sutures, dissolved in biocompatible carriers. These pharmaceuticals may be blended into a liquid delivery system at the time of manufacturing or, depending upon the product, may be added later by a physician at the time of use. Injection of the liquid product subcutaneously or intramuscularly through a small gauge needle, or placement into accessible tissue sites through a cannula, causes displacement of the carrier with water in the tissue fluids, and a subsequent precipitate to form from the polymer into a solid film or implant. Examples of such drug delivery systems include ATRIX'S ELIGARD, ATRIDOX/DOXIROBE, ATRISOR, FREEFLOW/ATRISORB-D FREEFLOW, bone growth products, and others as described in the following published US and PCT patent applications assigned to Atrix Laboratories Inc.: U.S. RE37950; U.S. Pat. No. 6,630,155; U.S. Pat. No. 6,566,144; U.S. Pat. No. 6,610,252; U.S. Pat. No. 6,565,874; U.S. Pat. No. 6,528,080; U.S. Pat. No. 6,461,631; U.S. Pat. No. 6,395,293; U.S. Pat. No. 6,261,583; U.S. Pat. No. 6,143,314; U.S. Pat. No. 6,120,789; U.S. Pat. No. 6,071,530; U.S. Pat. No. 5,990,194; U.S. Pat. No. 5,945,115; U.S. Pat. No. 5,888,533; U.S. Pat. No. 5,792,469; U.S. Pat. No. 5,780,044; U.S. Pat. No. 5,759,563; U.S. Pat. No. 5,744,153; U.S. Pat. No. 5,739,176; U.S. Pat. No. 5,736,152; U.S. Pat. No. 5,733,950; U.S. Pat. No. 5,702,716; U.S. Pat. No. 5,681,873; U.S. Pat. No. 5,660,849; U.S. Pat. No. 5,599,552; U.S. Pat. No. 5,487,897; U.S. Pat. No. 5,368,859; U.S. Pat. No. 5,340,849; U.S. Pat. No. 5,324,519; U.S. Pat. No. 5,278,202; U.S. Pat. No. 5,278,201; US 20020114737, US 20030195489; US 20030133964; US20010042317; US 20020090398; US20020001608; and US2001042317.

Atrix Laboratories Inc. also developed technology for the non-oral transmucosal delivery of drugs over a time period from minutes to hours. For example, Atrix's BEMA (BioerodibleMuco-Adhesive Disc) drug delivery system comprises pre-formed bioerodible discs for local or systemic delivery. Examples of such drug delivery systems include those as described in U.S. Pat. No. 6,245,345.

Other drug delivery systems developed by Atrix Laboratories Inc. focus on topical drug delivery. For example, SMP (Solvent Particle System) allows the topical delivery of highly water-insoluble drugs. This product allows for a controlled amount of a dissolved drug to permeate the epidermal layer of the skin by combining the dissolved drug with a microparticle suspension of the drug. The SMP™ system works in stages whereby: 1) the product is applied to the skin surface; 2) the product near follicles concentrates at the skin pore; 3) the drug readily partitions into skin oils; and 4) the drug diffuses throughout the area. Yet another product, BCP (Biocompatible Polymer System) provides a non-cytotoxic gel or liquid that is applied as a protective film for wound healing. Examples of these systems include ORA-JEL-ULTRA MOUTH SORE MEDICINE as well as those as described in the following published U.S. patents and applications assigned to Atrix Laboratories Inc.: U.S. Pat. No. 6,537,565; U.S. Pat. No. 6,432,415; U.S. Pat. No. 6,355,657; U.S. Pat. No. 5,962,006; U.S. Pat. No. 5,725,491; U.S. Pat. No. 5,722,950; U.S. Pat. No. 5,717,030; U.S. Pat. No. 5,707,647; U.S. Pat. No. 5,632,727; and US 20010033853.

MicroCHIPS has developed its core technology for drug delivery by hermetically sealing small quantities of drug in the microreservoirs, and releasing that drug on schedule or demand. Precise, long-term drug delivery can be achieved by using individual microreservoirs to store and hermetically protect the drug, microchip activation to release the drug, and telemetry to both control and communicate release. This creates the opportunity for more accurate dosing, reduced cost-of-care, improved patient compliance and, ultimately, improved patient outcomes.

TARIS has developed an approach designed to deliver therapeutics directly to the bladder continuously, and provide sustained relief of symptoms for periods of weeks to months. TARIS' proprietary delivery system, administered to patients via existing, minimally invasive procedures (e.g. catheterization, flexible cystoscopy), combines three proven strategies in drug delivery: 1) Osmotic delivery; 2) Shape memory technology; and 3) Implant retention. TARIS' lead program is LiRIS (Lidocaine Releasing Intravesical System), which is in development for the treatment of Interstitial Cystitis (IC). Methods of administration of the active agents of the present disclosure may include those described above, as well as other methods that are known to one of skill in the art.

One of skill in the art recognizes that the concentration of the active agent in any of the aforementioned dosage forms and compositions can vary a great deal and will depend on a variety of factors, including the type of composition or dosage form, the corresponding mode of administration, the nature and activity of the specific active agent, and the intended drug release profile. Preferred dosage forms contain a unit dose of active agent, i.e., a single therapeutically effective dose. For creams, ointments, etc., a "unit dose" requires an active agent concentration that provides a unit dose in a specified quantity of the formulation to be applied. The unit dose of any particular active agent will depend, of course, on the active agent and on the mode of administration. Similarly, the affinity of NK2R agonists for the NK2R is expected to differ substantially between each structurally distinct NK2R agonist, and doses and concentrations of each NK2R agonist should be adjusted based on comparison of each distinct NK2R agonist's affinity for the NK2R to the affinity of, for example, DTI-100, NKA, and beta-Ala-NKA (4-10) for the NK2R when deciding on an appropriate dose for each distinct NK2R agonist.

NK2R affinity is easily determined using standard receptor binding protocols (Burcher paper reference), such as generating concentration displacement curves of radiolabeled NKA to establish pD. Using similar if not identical binding conditions, the binding affinity of certain of the NK2R agonists of the present disclosure including, for example, DTI-100, NKA, and beta-Ala-NKA(4-10) can be established. If the NK2R agonist of choice has a lower affinity than DTI-100, NKA, or beta-Ala-NKA(4-10) for the NK2R, then higher plasma concentrations would need to be achieved when dosing the particular NK2R agonist than the concentrations observed for DTI-100, NKA, or beta-Ala-NKA(4-10). On the other hand, if the particular NK2R agonist has a higher affinity than DTI-100, NKA, or beta-Ala-NKA(4-10) for the NK2R, then lower plasma concentrations can be used to achieve therapeutic benefit when dosing with the particular NK2R agonist. For example, if the particular NK2R agonist has an affinity 10× lower than DTI-100, then the plasma concentration to achieve a therapeutic benefit (e.g. pM) for the particular NK2R agonist can be 10× higher than DTI-100.

For doing of active agents exhibiting NK2 receptor agonist activity and having a rapid-onset and short duration of action, regardless of the formulation or mode of delivery, pharmacokinetic profiles (i.e. $C_{max}$, $T_{max}$, and $T_{1/2}$) can be provided that are similar to those produced by i.v. doses of DTI-100 as described herein to produce a therapeutic benefit, (e.g., in the range of about 0.001 µg/kg to about 300 µg/kg with compensation for NK2R affinity).

Thus, the unit dose for oral administration for active agents exhibiting NK2 receptor agonist activity and having a rapid-onset and short duration of action can be in the range of from about 1 nanogram (ng) to about 10,000 mg, in the range of from about 100 ng to about 5,000 mg; and for local administration, suitable unit doses may be lower. The unit dose for oral administration can be greater than about 1 mg, about 5 mg, about 10 mg, about 20 mg, about 30 mg, about 40 mg, about 50 mg, about 100 mg, about 200 mg, about 300 mg, about 400 mg, about 500 mg, about 1,000 mg, about 1,500 mg, about 2,000 mg, about 2,500 mg, about 3,000 mg, about 3,500 mg, about 4,000 mg, about 4,500 mg, about 5,000 mg, about 5,500 mg, about 6,000 mg, about 6,500 mg, about 7,000 mg, about 7,500 mg, about 8,000 mg, about 8,500 mg, about 9,000 mg, or about 9,500 mg. One of ordinary skill in the art of pharmaceutical formulation can also readily deduce suitable unit doses for other types of active agents that may be incorporated into a dosage form of the present disclosure.

For active agents exhibiting NK2 receptor agonist activity, including rapid-onset compounds exhibiting NK2 receptor agonist activity and/or short acting compounds exhibiting NK2 receptor agonist activity, the unit dose for transmucosal, topical, transdermal, and parenteral administration can be in the range of from about 1 ng to about 10,000 mg, in the range of from about 100 ng to about 5,000 mg. The unit dose for transmucosal, topical, transdermal, and parenteral administration can be greater than about 1 ng, about 5 ng, about 10 ng, about 20 ng, about 30 ng, about 40 ng, about 50 ng, about 100 ng, about 200 ng, about 300 ng, about 400 ng, about 500 ng, about 1 µg, about 5 µg, about 10 µg, about 20 µg, about 30 µg, about 40 µg, about 50 µg, about 100 µg, about 200 µg, about 300 µg, about 400 µg, about 500 µg, about 1 mg, about 5 mg, about 10 mg, about 20 mg, about 30 mg, about 40 mg, about 50 mg, about 100 mg, about 200 mg, about 300 mg, about 400 mg, about 500 mg, about 1,000 mg, about 1,500 mg, about 2,000 mg, about 2,500 mg, about 3,000 mg, about 3,500 mg, about 4,000 mg, about 4,500 mg, about 5,000 mg, about 5,500 mg, about 6,000 mg, about 6,500 mg, about 7,000 mg, about 7,500 mg, about 8,000 mg, about 8,500 mg, about 9,000 mg, or about 9,500 mg. Those of ordinary skill in the art of pharmaceutical formulation can readily deduce suitable unit doses for other compounds exhibiting NK2 receptor agonist activity, including rapid-onset compounds exhibiting NK2 receptor agonist activity and/or short acting compounds exhibiting NK2 receptor agonist activity. One of ordinary skill in the art of pharmaceutical formulation can also readily deduce suitable unit doses for other types of active agents that may be incorporated into a dosage form of the invention.

For active agents exhibiting NK2 receptor agonist activity, including rapid-onset compounds exhibiting NK2 receptor agonist activity and/or short acting compounds exhibiting NK2 receptor agonist activity, the unit dose for intrathecal administration can be in the range of from about 1 fg to about 1 mg, in the range of from about 100 fg to about 1 ng. The unit dose for intrathecal administration can be greater than about 1 fg, about 5 fg, about 10 fg, about 20 fg, about 30 fg, about 40 fg, about 50 fg, about 100 fg, about 200 fg, about 300 fg, about 400 fg, about 500 fg, about 1 pg, about 5 pg, about 10 pg, about 20 pg, about 30 pg, about 40 pg, about 50 pg, about 100 pg, about 200 pg, about 300 pg, about 400 pg, about 500 pg, about 1 ng, about 5 ng, about 10 ng, about 20 ng, about 30 ng, about 40 ng, about 50 ng, about 100 ng, about 200 ng, about 300 ng, about 400 ng, about 500 ng, about 1 µg, about 5 µg, about 10 µg, about 20 µg, about 30 µg, about 40 µg, about 50 rig, about 100 µg, about 200 µg, about 300 µg, about 400 µg, or about 500 µg. Those of ordinary skill in the art of pharmaceutical formulation can readily deduce suitable unit doses for other active agents exhibiting NK2 receptor agonist activity, including rapid-onset compounds exhibiting NK2 receptor agonist activity and/or short acting compounds exhibiting NK2 receptor agonist activity. One of ordinary skill in the art of pharmaceutical formulation can also readily deduce suitable unit doses for other types of active agents that may be incorporated into a dosage form of the invention.

A therapeutically effective amount of a particular active agent administered to a given individual will, of course, be dependent on a number of factors, including the concentration of the specific active agent, composition or dosage form, the selected mode of administration, the age and general condition of the individual being treated, the severity of the individual's condition, and other factors known to the prescribing physician. However, one of skill in the art would readily recognize that the therapeutically effective amount of a particular active agent must be selected so as to allow for as-needed administration, as defined further herein.

With an immediate release dosage form, as-needed administration may involve drug administration immediately prior to when commencement of emptying of the bladder or bowel would be desirable. The as-need administration can range from about 0 minutes to about 40 minutes prior to the desired emptying, from about 0 minutes to about 20 minutes prior, or about 0 minutes to about 5 minutes prior.

In another embodiment, a packaged kit is provided that contains the pharmaceutical formulation to be administered, i.e., a pharmaceutical formulation containing a therapeutically effective amount of a selected active agent for the treatment of loss of or decrease in voluntary control of voiding and/or defecation or having urinary and/or fecal incontinence, a container, preferably sealed, for housing the formulation during storage and prior to use, and instructions for carrying out drug administration in a manner effective to treat the loss or decrease in control and/or the incontinence. The instructions will typically be written instructions on a package insert and/or on a label. Depending on the type of formulation and the intended mode of administration, the kit may also include a device for administering the formulation. The formulation may be any suitable formulation as described herein. The active agent can be a rapid onset and short acting NK2R agonist, or a pharmaceutically acceptable salt thereof. The rapid onset and short acting NK2R agonist can be [Lys5,MeLeu9,Nle10]-NKA(4-10) (SEQ ID NO: 1), or a pharmaceutically acceptable salt thereof. The manner for treating the loss of or decrease in voluntary control of voiding and/or defecation or having urinary and/or fecal incontinence may be administration on an as-needed basis to treat the urinary voiding and/or defecation dysfunction. The as-need basis can range from about 0 minutes to about 40 minutes prior to when the voiding and/or defecation is desired, from about 0 minutes to about 20 minutes prior to when the voiding and/or defecation is desired, or from about 0 minutes to about 5 minutes prior to when the voiding and/or defecation is desired.

The kit may contain multiple formulations of different dosages of the same agent. The kit may also contain multiple formulations of different active agents. The kit may contain formulations suitable for sequential, separate and/or simultaneous use in the treatment of urinary voiding and/or defecation dysfunction, and instructions for carrying out drug administration where the formulations are administered sequentially, separately and/or simultaneously in the treatment of urinary voiding and/or defecation dysfunction. The parts of the kit may be independently held in one or more containers—such as bottles, syringes, plates, wells, blister packs, or any other type of pharmaceutical packaging.

The packaged kit may further comprise a therapeutically effective amount of a NK2R antagonist, or a pharmaceutically acceptable salt thereof, to terminate the majority of the effects of the NK2R agonist within about 10 minutes, wherein the NK2R antagonist has a duration of action of less than about 4 hours. The NK2R antagonist can have a duration of action of less than about 3 hours. The NK2R antagonist can have a duration of action of less than about 2 hours. The NK2R agonist can be [Lys5,MeLeu9,Nle10]-NKA(4-10) (SEQ ID NO: 1), or a pharmaceutically acceptable salt thereof.

In the packaged kit, the NK2R agonist and the NK2R antagonist can be formulated together in a single pharmaceutical formulation and an onset of action of the NK2R antagonist can be longer than the rapid onset of the NK2R agonist. The onset of action of the NK2R antagonist can be longer than the rapid onset of the NK2R agonist to terminate the majority of the effects of the NK2R agonist within about 5 minutes. The onset of action of the NK2R antagonist can be longer than the rapid onset of the NK2R agonist to terminate the majority of the effects of the NK2R agonist within about 10 minutes.

In the packaged kit, the NK2R agonist and the NK2R antagonist can be formulated separately in two separate pharmaceutical formulations, wherein the NK2R antagonist is administered subsequent to administration of the NK2R agonist, and wherein an onset of action of the NK2R antagonist can range from about 0 to about 10 minutes. The onset of action of the NK2R antagonist can range from about 0 to about 5 minutes.

In another embodiment, a pharmaceutical formulation is provided for treating one or both of urinary voiding and defecation dysfunction in a mammal in need of treatment on an as-needed basis, which includes a therapeutically effective amount of a rapid onset and short acting NK2R agonist, or a pharmaceutically acceptable salt thereof, and a carrier for administration of the NK2R agonist to the mammal on the as-needed basis. The pharmaceutical formulation can also be useful for inducing voiding in a mammal without an actual voiding and/or defecation dysfunction. The NK2R agonist can be [Lys5,MeLeu9,Nle10]-NKA(4-10) (SEQ ID NO: 1), or a pharmaceutically acceptable salt thereof. The carrier for administration may be any suitable formulation as described herein. The as-need administration can range from about 0 minutes to about 40 minutes prior to when the voiding and/or defecation is desired, from about 0 minutes to about 20 minutes prior to when the voiding and/or defecation is desired, or from about 0 minutes to about 5 minutes prior to when the voiding and/or defecation is desired.

The pharmaceutical formulation may further comprise a therapeutically effective amount of a NK2R antagonist, or a pharmaceutically acceptable salt thereof, wherein the onset of action of the NK2R antagonist is longer than the rapid onset of the NK2R agonist to terminate the majority of the effects of the NK2R agonist within about 15 minutes after occurrence of the one or both of urinary voiding and defecation, wherein the NK2R antagonist has a duration of action of less than about 4 hours. The NK2R antagonist can have a duration of action of less than about 3 hours. The NK2R antagonist can have a duration of action of less than about 2 hours. The onset of action of the NK2R antagonist can be longer than the rapid onset of the NK2R agonist to terminate the majority of the effects of the NK2R agonist within about 10 minutes after occurance of the one or both of urinary voiding and defecation. The onset of action of the NK2R antagonist can be longer than the rapid onset of the NK2R agonist to terminate the majority of the effects of the NK2R agonist within about 5 minutes after occurance of the one or both of urinary voiding and defecation.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

General Methods: NK2 Receptor Agonists for on-Demand Urinary Voiding and Defecation in Multiple Animal Species The following methods were used to determine the efficacy, specificity, onset of action and the duration of action of various NK2R agonists on bladder and gastrointestinal (GI) function in a rat model of acute spinal cord injury. In addition, the reproducibility of multiple dosing and the pharmacodynamic (PD) responses of administering the NK2R agonists via various routes of administration were explored. Further, the effects on urinary voiding and defecation after administration of the NK2R agonist [Lys5, MeLeu9,Nle10]-NKA(4-10) (SEQ ID NO: 1; DTI-100) to beagle dogs was investigated. In summary, DTI-100 was shown to be a selective NK2R agonist that produced dose dependent increases in bladder and colorectal contractions consistent with use of DTI-100 for inducing voiding of urine and defecation of feces. The onset of action of DTI-100 is rapid with a short duration. Repeated dosing of DTI-100 produced reproducible increases in bladder pressure without significant reduction in response. The effects of DTI-100 on bladder and colorectal contractions were observed for various routes of administration.

Rat Methods:

General: In vivo studies were performed in anesthetized, acutely spinalized (T9-10 level) rats (N=37) or spinally intact (N=3) rats. Adult female Sprague Dawley rats (Charles River, N.C.; 250-300 g) were housed at an AAALAC approved facility in cages (3/cage) with free access to water and food in a colony room that was maintained on a 12 hr/12 hr light/dark cycle 1-2 weeks before the experiment. Rats were anesthetized with urethane (1.2-1.4 g/kg subcutaneous injection). Surgical procedures were then performed with the addition of isoflurane anesthesia (0.05-1.5% in O2) as the full anesthetic effect of urethane takes about 1-2 hrs.

A catheter filled with heparinized saline (50 unit/ml) was inserted into the carotid artery and connected to a pressure transducer for measurement of blood pressure and heart rate. A catheter was inserted into the jugular vein for intravenous (i.v.) administration of drugs. In order to transect the spinal cord, the skin and muscle on the dorsal side at the level of the lower thoracic vertebrae were incised, and the spinal cord was carefully exposed by a laminectomy and transected at the T8-T10 spinal level. Gelfoam was placed at the incision site and the muscle and skin overlying the vertebrae were closed with wound clips. The spinal cord was cut at least 60 min before starting the experimental protocol. Blood pressure, bladder pressure and colorectal pressure signals were amplified and displayed on a computer using LABCHART (AD Instruments, Colorado Springs, Colo.).

Bladder Contractility: For isovolumetric recordings of bladder pressure a saline-filled polyethylene tubing with a flared tip (PE 50®) catheter was inserted into the bladder and secured in place at the dome. This catheter was used to slowly infuse saline (0.2-0.3 ml/min by an infusion pump (PHD2000 infusion, Harvard Apparatus, Holliston, Mass.) to determine the bladder capacity. The bladder capacity was determined as the volume necessary to fill the bladder to the leak point pressure (i.e. volume required to produce voiding). The bladder was then emptied, the external urethra occluded and the bladder filled to 70% capacity. This method produced a stable baseline pressure in which drug induced changes in bladder contractility could be measured. Peak pressure responses, time to peak, and time to return to near baseline values (within 5 mmHg of baseline; i.e. duration of action) after vehicle and drug administration were measured.

Colorectal Contractility: Colorectal pressures were measured via a latex balloon catheter (length 3-5 cm) inserted (~4 cm) into the distal rectal/colon region. The catheter was connected to a pressure monitoring system. The pressure in the balloon catheter was slowly increase to 15-20 mmHg by infusing saline (0.3-0.7 ml total volume) and this pressure was maintained throughout the study. This allowed drug induced changes in colorectal pressure to be monitored. Parameters measured include peak colorectal pressure response, duration of time above baseline activity (in the $1^{st}$ 5 min after drug administration), area under the curve (measured during the $1^{st}$ 5 min after drug administration) and the number of contractile events after vehicle and drug administration.

Dosing: Responses to saline i.v. were given to ensure stable baseline pressures and lack of response to saline (vehicle control for DTI-100) at the start of each protocol and periodical throughout the experiment. DTI-100 was given in dose range of 0.01-100 µg/kg. The NK1R antagonist, Spantide I (solubilized in saline) and NK2R antagonist GR159897 (solubilized at 50 mM in DMSO and then diluted in saline) were given at a 1 mg/kg dose. Neurokinin A (NKA) and (betaAla8)NKA(4-10) were given at doses 1-100 µg/kg. Additional routes of drug administration explored included, intramuscular, subcutaneous, and sublingual. [Lys5,MeLeu9,Nle10]-NKA(4-10) (SEQ ID NO: 1) or "DTI-100", Spantide I, GR159897, Neurokinin A, and (BetaAla8)NKA(4-10) were obtained from TOCRIS R&D SYSTEMS, Inc. (Minneapolis, Minn.).

Data analysis: Data were examined qualitatively and quantitatively. The mean, standard deviation and standard error of the mean were calculated using MICROSOFT EXCEL. One way ANOVA tests were performed with PRISM 5 for WINDOWS (Graphpad Software, Inc., La Jolla, Calif.) and unpaired and paired t-tests were performed in EXCEL. P<0.05 was considered as statistically significant.

Dog Methods:

General: Beagle dogs (6-11 kg, purpose-bred and experimentally naïve) were housed at an AAALAC approved facility in cages (1/cage) with access to water and food. All animal activities were performed in compliance with USDA guidelines. Animals were monitored for 5 days prior to dosing to ensure adequate health. An Institutional Animal Care and Use Committee approved all protocols used in this study.

Treatments and Dosing: Four treatment groups were included in this study: Saline, 1 µg/kg DTI-100, 10 µg/kg DTI-100, and 30 µg/kg DTI-100. Each treatment group consisted of 2 animals (1 male, 1 female). Awake, freely moving animals were dosed individually via i.v. bolus administration. For each treatment group, four doses per day were administered at four hour intervals during the day for five consecutive days. A total of 20 doses were administered per animal over the 5 day period.

Observations: Voiding behavior was observed and recorded by trained professionals. Animals were monitored prior to each dose, continuously for 10 minutes following each dose and once again between 30-60 minutes following each dose, A urination event was recorded when the animal assumed a typical voiding posture and urine was voided. A defecation event was recorded when the animal assumed a typical defecation posture and feces were voided.

Data analysis: Data were reported as the number of events occurring in response to a specific dose of DTI-100 within a specific period of time.

Example 2

Figure 3:
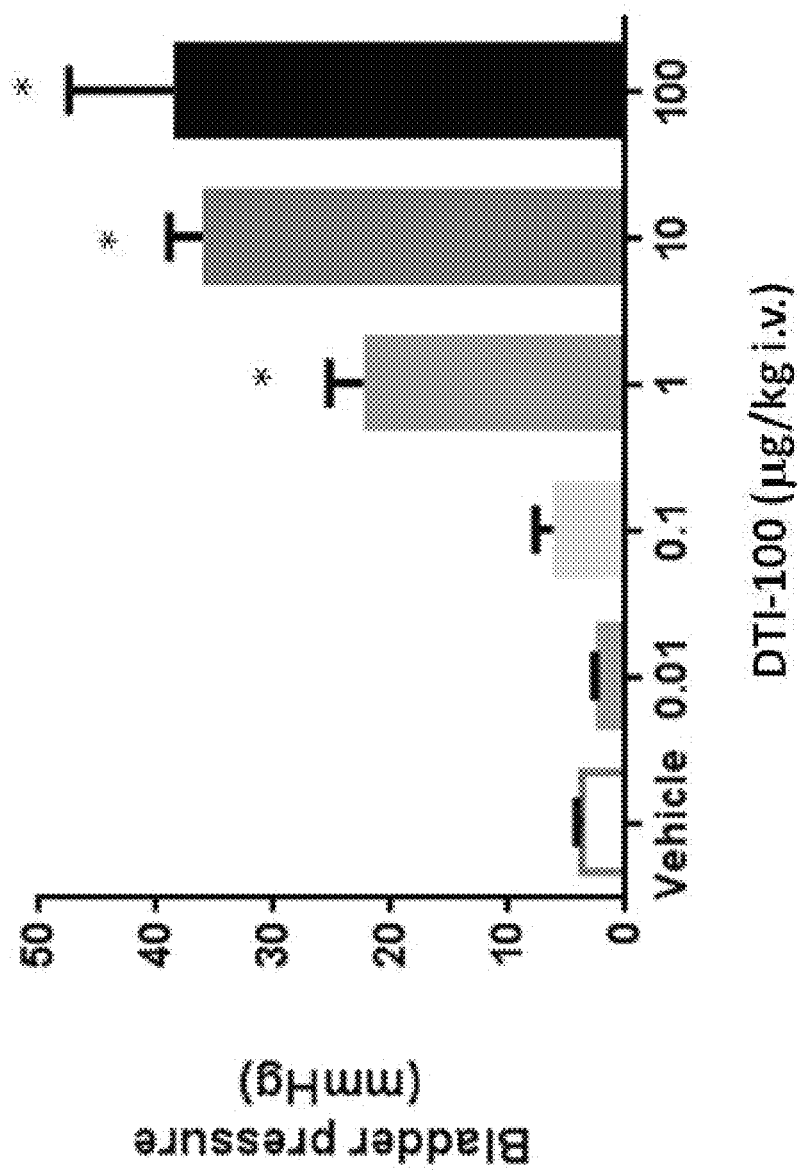
FIG. 3 is a bar graph showing the effects of DTI-100 on bladder contraction in anesthetized acutely spinalized female rats according to one or more embodiments of the presently disclosed subject matter. The bars represent the mean of the peak bladder pressure response (mmHg) in 15 rats in response to Vehicle and increasing intravenous doses of DTI-100 (0.01 µg/kg, N=2), (0.1 µg/kg, N=5), (1 µg/kg, N=8), (10 µg/kg, N=15), and (100 µg/kg, N=4). The (*) indicates values significantly different from the vehicle.

Effective Doses, Onset of Action and Duration of Action of DTI-100 to Induce Bladder Contraction DTI-100 induced a dose related increase in bladder pressure in acutely spinalized, anesthetized female rats (FIG. 3) Specifically FIG. 3 is a bar graph showing the effects of DTI-100 on bladder contraction in anesthetized acutely spinalized female rats. DTI-100 produced a dose related increase in bladder pressure. The bars represent the mean+ S.E. of the peak pressure response. (*) indicates values significantly different from the vehicle (p<0.05 using one-way ANOVA followed by Bonferroni's Multiple Comparison post-test); one-way ANOVA [F (5,43)=222, p=0.0001]. The post hoc Bonferonni's multiple comparison test confirmed that 1, 10 and 100 µg/kg doses of DTI-100 produced a significant increase in bladder pressure compared to vehicle. Doses of 0.01 and 0.1 µg/kg of DTI-100 were not statistically different compared to vehicle. The number of rats and doses of DTI-100 in each group=2 (0.01 mg/kg), 5 (0.1 µg/kg), 8 (1 µg/kg), 15 (10 µg/kg), and 4 (100 µg/kg).

Figure 4:
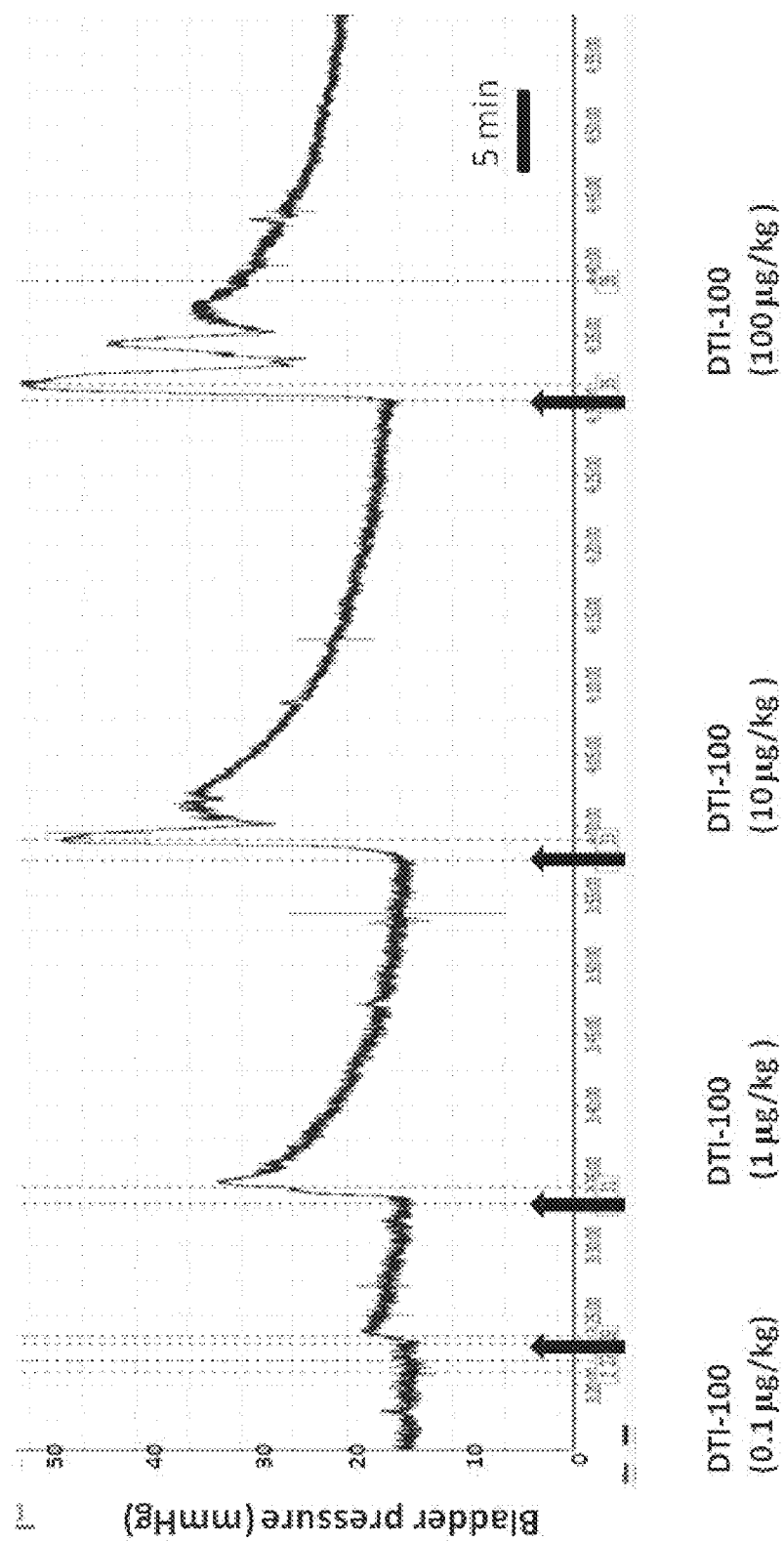
FIG. 4 is a graph showing the dose dependent increase in bladder pressure induced by the i.v. doses of DTI-100 described in FIG. 3 which produced an immediate increase in bladder pressure that peaked within 60 sec of administration. The arrows in FIG. 4 indicate the time each dose was administered.

The time taken for DTI-100 to produce the peak bladder pressure response was within 60 sec at all doses studied (FIG. 4). Specifically, FIG. 4 shows a dose dependent increase in bladder pressure induced by increasing i.v. doses of DTI-100 (ranging from 0.1-100 µg/kg) which produced an immediate increase in bladder pressure that peaked within 60 sec of administration. The arrows in FIG. 4 indicate the time each dose was administered. The bladder pressure responses returned to ~5 mmHg of the baseline within 10 min. The time taken for the bladder pressure to return to near pre-drug baseline (within 5 mmHg) values was within 10 min.

Figure 5:
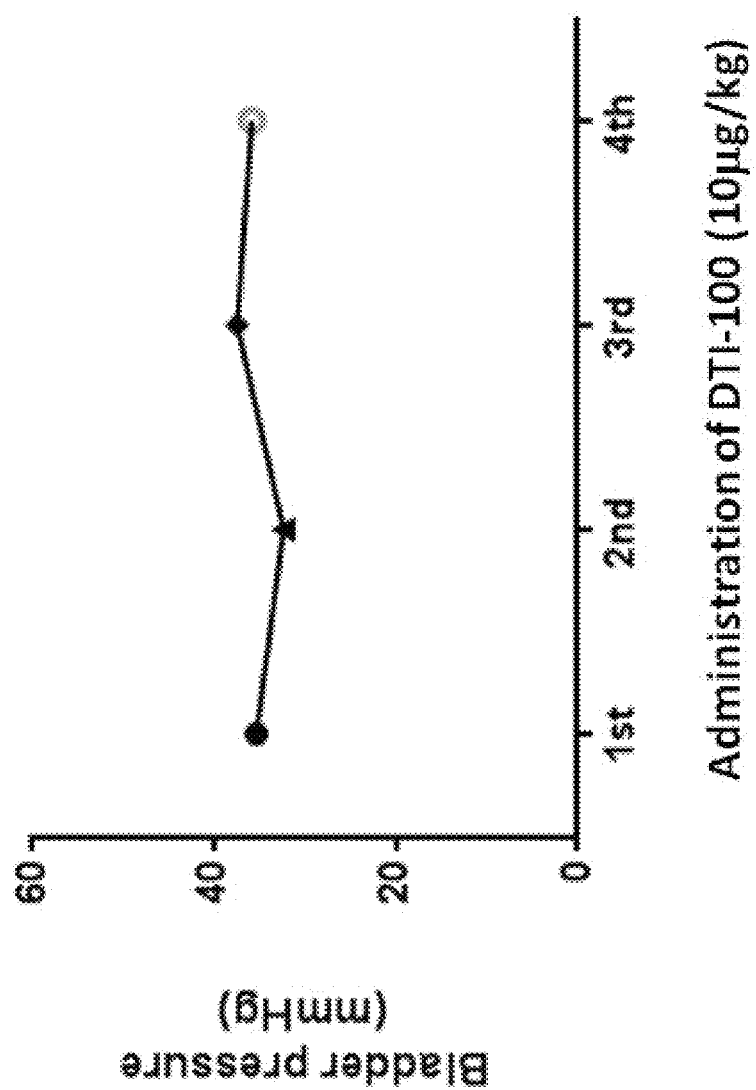
FIG. 5 is a graph showing that repeat intravenous dosing of DTI-100 (10 µg/kg) in anesthetized acutely spinalized female rats produced consistent and reproducible increases in bladder pressure according to one or more embodiments of the presently disclosed subject matter. The graph shows an example of the peak bladder pressure (mmHg) responses to repeat dosing (4 doses given at 1-2 hr intervals) in the same rat.

Repeated i.v. dosing of DTI-100 (10 µg/kg) produced reproducible increases in bladder pressure (FIG. 5) with no reduction of the response. FIG. 5 shows repeat dosing of DTI-100 (10 µg/kg i.v.) produced consistent and reproducible increases in bladder pressure. The graph shows an example of the peak bladder pressure responses to repeat dosing (4 doses given at 1-2 hr intervals) in the same rat.

These data demonstrate that DTI-100 contracts the bladder in a dose dependent manner and that the onset of action is rapid with a short duration of action. Furthermore, DTI-100 can be given repeatedly without significant loss of effect.

Example 3

Selectivity of DTI-100 for NK2 Receptors for Inducing Bladder Contraction

Figure 6A:
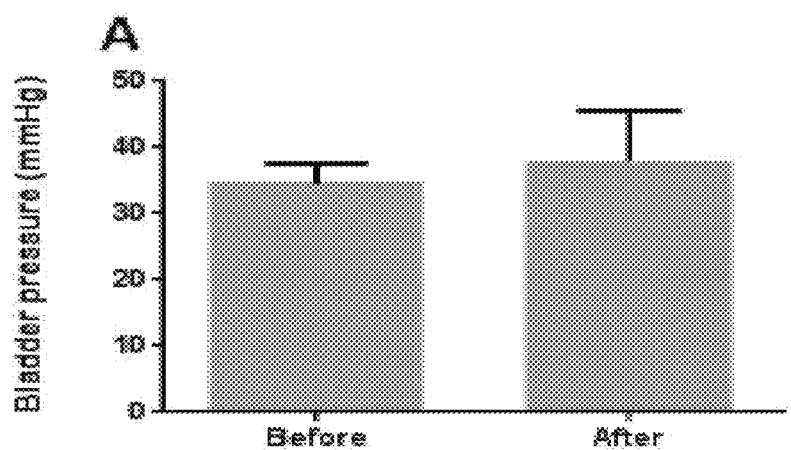
FIGS. 6A-6B are bar graphs showing DTI-100 induced increase in bladder pressure in anesthetized acutely spinalized female rats before and after administration of a NK1R antagonist (Spantide I) and a NK2R antagonist (GR159897) according to one or more embodiments of the presently disclosed subject matter. A) Peak bladder pressure response to DTI-100 was the same before (Before) and after (After) administration of NK1R antagonist, Spantide I (paired t-test, p=0.5255, N=4). B) Peak bladder pressure response to DTI-100 was significantly blocked after administration of NK2R antagonist GR159897 (paired t-test, p=0.0144, N=4).
Figure 6B:
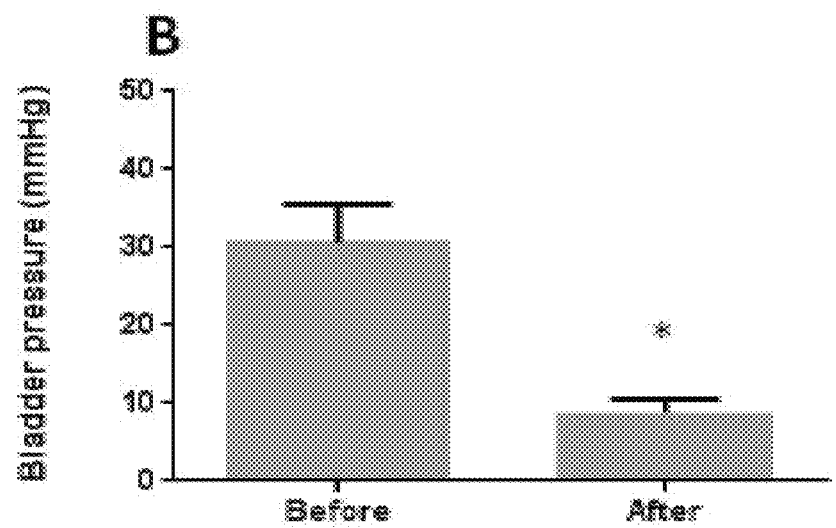

In order to verify the selectivity for DTI-100 for NK2 receptors, the DTI-100 induced increase in bladder pressure was examined before and after administration of a NK1R antagonist (Spantide I) and a NK2R antagonist (GR159897). The data in FIGS. 6A-6B show that DTI-100 (10 µg/kg) produced an increase in bladder pressure that was mediated via NK2 receptors. FIG. 6A shows the DTI-100 (10 µg/kg i.v.) response before and after administration of the NK1R antagonist Spantide I (paired t-test, p=0.5255, N=4) and FIG. 6B shows the DTI-100 (10 µg/kg i.v.) response before and after administration of the NK2R antagonist GR159897 (paired t-test, p=0.0144, N=4). Pre-administration of Spantide I did not reduce the effect of DTI-100 on bladder pressure, however pre-administration of GR159897 significantly blocked the bladder pressure increase to DTI-100. Administration of vehicle (saline or DMSO in saline) did not reduce the bladder pressure response to DTI-100. These data suggest that DTI-100 induces bladder contractility via NK2 receptors.

Example 4

Bladder Contractility Induced by NK2 Receptor Agonists

Figure 7:
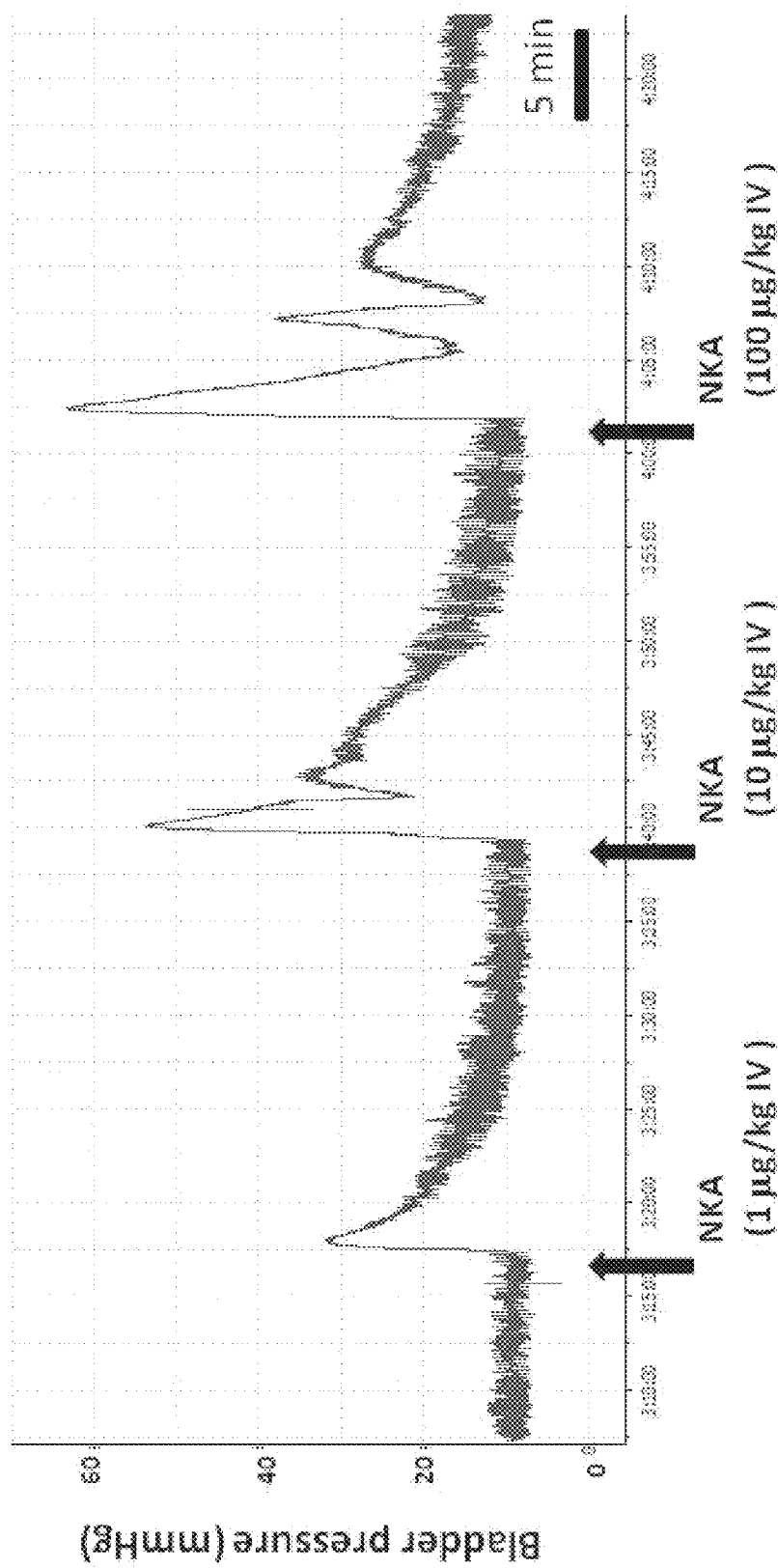
FIG. 7 is a graph showing the dose dependency of the increases in bladder pressure induced by the NK2R agonist NKA in anesthetized acutely spinalized female rats, taken from a single experiment according to one or more embodiments of the presently disclosed subject matter. Increasing i.v. doses of NKA ranging from 1-100 µg/kg (the arrows show the time that each dose was administered) produced an immediate increase in bladder pressure that peaked within 60 sec of administration.
Figure 8:
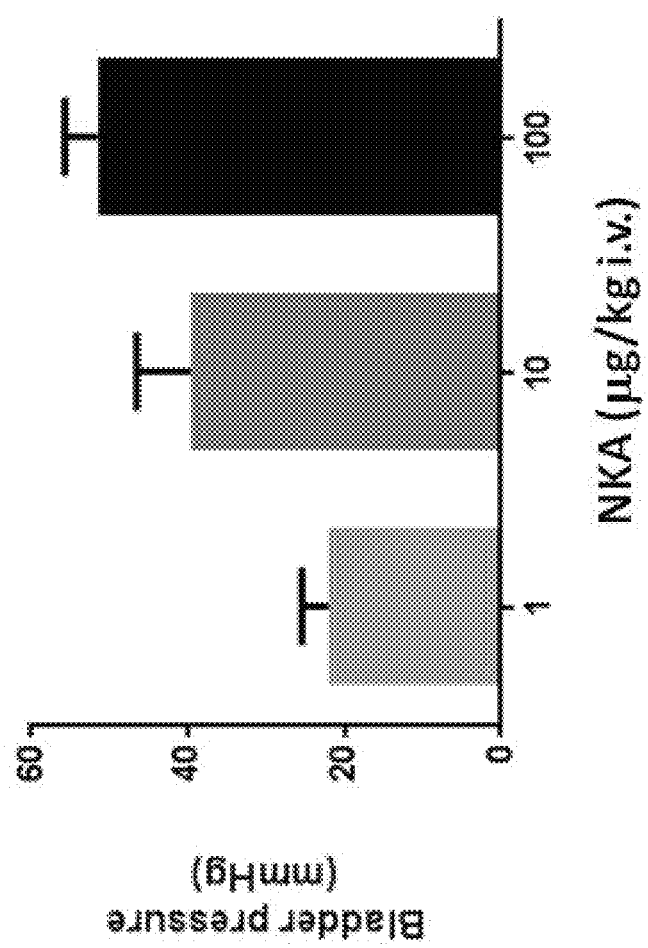
FIG. 8 is a bar graph showing the effects of NKA on bladder contraction in anesthetized acutely spinalized female rats according to one or more embodiments of the presently disclosed subject matter. The bars represent the mean of the peak bladder pressure response (mmHg) in 2-3 rats in response to increasing intravenous doses of NKA (1-100 µg/kg).

In addition to DT100, two other NK2R agonists, neurokinin A (NKA) and (betaAla8)NKA(4-10) were shown to produce increases in bladder pressure in experiments performed as described above. FIG. 7 and FIG. 8 show the dose dependency of the increases in bladder pressure induced by the NK2R agonist NKA. FIG. 7 is taken from a single experiment. FIG. 8 shows the peak bladder pressure responses (mean+S.E. of 2-3 rats). Increasing i.v. doses of NKA ranging from 1-100 µg/kg (the arrows in FIG. 7 show the time that each dose was administered) produced an immediate increase in bladder pressure that peaked within 60 sec of administration. Duration of action (time taken to return to near baseline) for NKA responses was less than 10 min. Similar results were obtained for (betaAla8)NKA(4-10); the time to peak was within 60 sec and the duration of action was less than 10 min (data not shown).

Example 5

Routes of Administration to Induce Urinary Voiding by NK2 Receptor Agonists

Figure 9A:
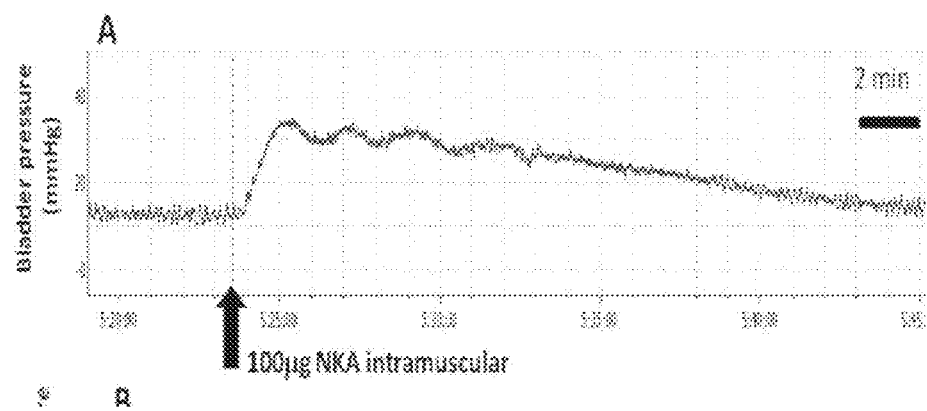
FIGS. 9A-9B are graphs illustrating examples of two different routes of administration (intramuscular and sublingual injections) of NK2R agonists in anesthetized acutely spinalized female rats to produce an increase in bladder pressure according to one or more embodiments of the presently disclosed subject matter. A) NKA (100 µg/kg) as given by intramuscular injection and B) DTI-100 (100 µg/kg) given by sublingual injection.
Figure 9B:
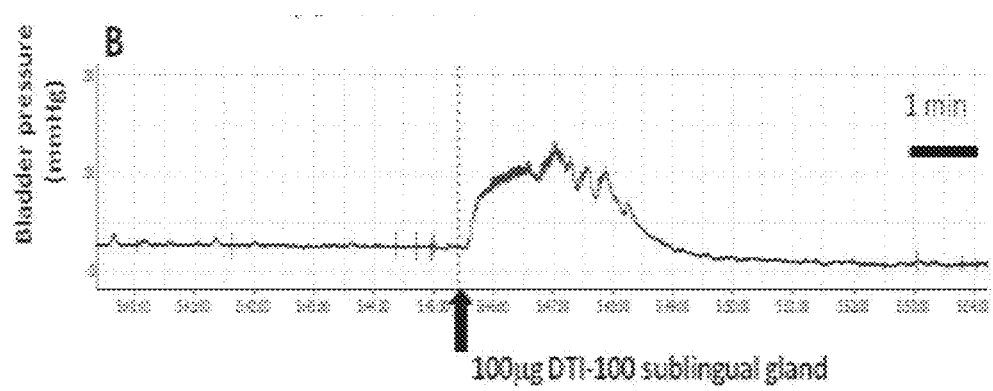

In addition to i.v. dosing of DTI-100, various routes of administration of NK2R agonists DTI-100 (10-100 µg/kg) and NKA (5-100 µg/kg) were examined. Intramuscular, subcutaneous, and sublingual injections of DTI-100 and NKA all showed an increase in bladder pressure. For example, IM administration of DTI 100 µg/kg resulted in an increase in bladder pressure of 12.6+2.1 mmHg, (man+S.E., N=3) with 182+19 sec (~3 min) time to peak and duration of 1133+22 sec (ie ~18 min). NKA (100 µg/kg) administered IM gave a similar drug response profile to DTI-100. Sublingual injections of DTI-100 or NKA produced an increase in bladder pressure (range 10-25 mmHg) within 2 min of drug administration. FIG. 9 illustrates examples of two different routes of administration (intramuscular and sublingual injections) of NK2R agonists to produce an increase in bladder pressure. Specifically, FIG. 9A shows NKA (100 µg/kg) as given by intramuscular injection and FIG. 9B shows DTI-100 (100 µg/kg) given by sublingual injection.

Example 6

Figure 10A:
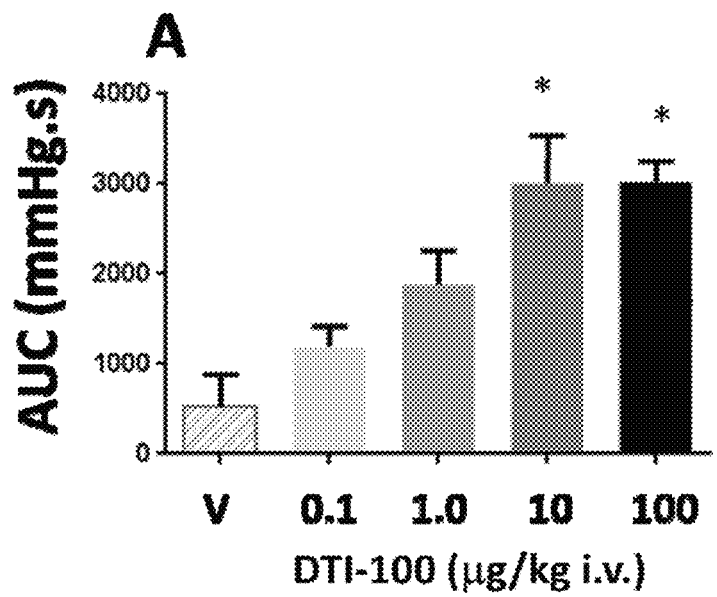
FIGS. 10A-10B are bar graphs showing the effects of DTI-100 on colorectal contractility in anesthetized acutely spinalized female rats according to one or more embodiments of the presently disclosed subject matter. A) DTI-100 induced dose dependent increases in AUC. B) DTI-100 induced dose dependent increases in duration of action. The bars represent the mean+S.E. of the peak pressure response and (*) indicates values significantly different from the vehicle (p<0.05 using one-way ANOVA followed by Bonferroni's Multiple Comparison post-test). The number of rats in each group=8 (V—which represents the baseline response), 5 (0.1 µg/kg), 6 (1 µg/kg), 8 (10 µg/kg), and 5 (100 µg/kg).
Figure 10B:
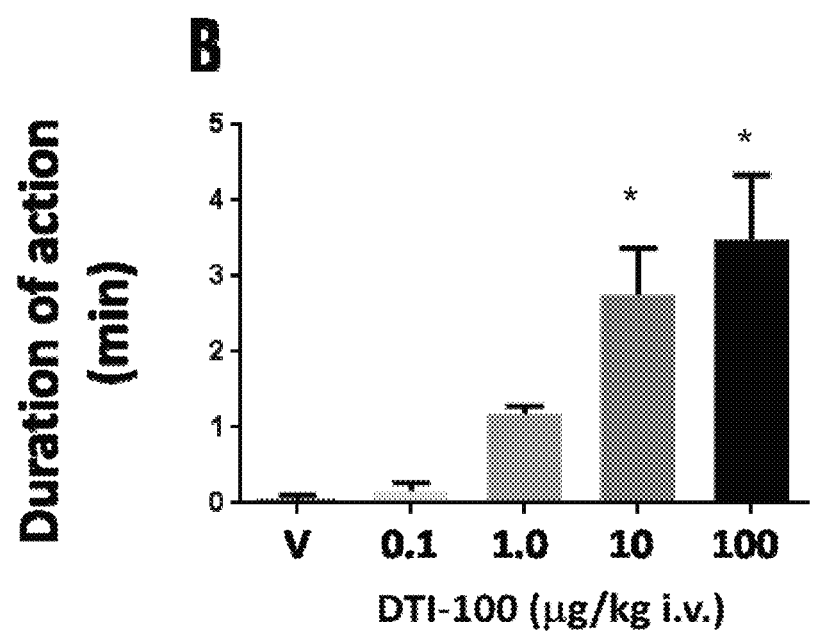

Effective Doses, Onset of Action, and Duration of Action of DTI-100 to Induce Colorectal Contractions DTI-100 produced an increase in colorectal activity in both intact and acutely spinalized rats. The effects of DTI-100 on colorectal contractility are shown in FIGS. 10A-10B. FIG. 10A shows DTI-100 induced dose dependent increases in AUC, and FIG. 10B shows DTI-100 induced dose dependent increases in duration of action. The bars represent the mean+S.E. of the peak pressure response and (*) indicates values significantly different from the vehicle (p<0.05 using one-way ANOVA followed by Bonferroni's Multiple Comparison post-test). The number of rats in each group was 8 (V—which represents the baseline response), 5 (0.1 µg/kg), 6 (1 µg/kg), 8 (10 µg/kg), and 5 (100 µg/kg). Doses of DTI-100 produced a dose related increase in colorectal activity that occurred within 60 sec of drug administration. The AUC significantly increased with increasing doses (one way ANOVA [F (4,27)=10.15, p=0.0001]). Doses of 10 and 100 µg/kg were significantly different compared to vehicle and the 0.01 µg/kg dose, as determined by Bonferroni's multiple comparison post-test (FIG. 10A). The duration of action (expressed as percentage of time above threshold in the $1^{st}$ 5 min after dosing) increased in a dose related manner (one way ANOVA [F (4,26)=9.182, p=0.0001]) (FIG. 10B).

These data demonstrate that DTI-100 induces colorectal contraction in a dose dependent manner and that the onset of action is rapid with a dose related increase in duration of action.

Example 7

Selectivity of DTI-100 for NK2 Receptors to Induce Colorectal Contractions

In order to verify the selectivity of DTI-100 for NK2 receptors, the DTI-100 induced increase in colorectal activity was examined before and after administration of Spantide I (NK1R antagonist) and GR159897 (NK2R antagonist). Administration of vehicle (saline or DMSO in saline) did not change colorectal activity. Pre-administration of Spantide I did not reduce the effect of DTI-100 on colorectal activity (data not shown), however pre-administration of GR159897 significantly blocked the bladder pressure increase produced by DTI-100 (FIG. 11). FIGS. 11A-11B are graphs showing the DTI-100 induced increase in colorectal activity before (A) and after (B) administration of GR159897 (NK2R antagonist). DTI-100 produced a significant increase in colorectal activity that was mediated via NK2 receptors. FIG. 11A shows the control response to DTI-100 (10 µg/kg) given at the time indicated by the arrow. FIG. 11B shows the lack of response to DTI-100 (10 µg/kg) when given 5 min after administration of the NK2R antagonist, GR159897 (1 mg/kg, i.v).

Increases in colorectal pressure were also observed with neurokinin A (N=1, 10-100 µg/kg i.v.) that produced similar increases in colorectal pressure and duration of action compared to DTI-100 (data not shown).

Example 8

Routes of Administration for On-Demand Defecation

In addition to i.v. dosing of DTI-100, the effect on colorectal pressure was also examined for other routes of administration of DTI-100. Specifically, subcutaneous and sublingual injections of DTI-100 (10-100 µg/kg) produced an increase in colorectal pressure that generally followed the bladder pressure profiles for time to onset and duration when DTI-100 was given by the same routes of administration.

Example 9

On-Demand Urinary Voiding and Defecation in the Beagle Dog

Eight dogs (four treatment groups, N=2 per group) were administered saline or DTI-100 as described herein above in Dog Methods. These data are summarized below in Table I. Each treatment group (saline, 1, 10, 30 µg/kg) included 40 total doses over the 5 day study (2 animals per group, 20 doses per animal). Whereas no urination or defecation events were observed following saline administration, doses of 10 and 30 µg/kg elicited events following 85-98% of doses. Animals receiving i.v. DTI-100 (1 µg/kg) urinated once and defecated twice within 10 minutes of DTI-100 administration. These three events occurred on response to DTI-100 administration, but intermittently across all combined 40 injections during the 5 day study. Animals receiving i.v. DTI-100 (10 µg/kg) urinated within 1-3 minutes following dosing in response to 39/40 total doses. These same animals defecated within 2-5 minutes following dosing in response to 34/40 total doses. Animals receiving i.v. DTI-100 (30 µg/kg) urinated within 1-3 minutes of dosing in response to 39/40 total doses. These same animals defecated within 2-5 minutes of dosing in response to 39/40 total doses. No voiding was observed in any animals after 5-10 minutes following dosing or at the 30-60 minute observation point.

TABLE I

The number of urination or defecation events observed in beagle dogs within 5 minutes following dosing of saline or DTI-100.

| Dose (µg/kg) | Urination (# events) | (%) | Defecation (# events) | (%) |
|---|---|---|---|---|
| Saline | 0/40 | 0 | 0/40 | 0 |
| 1 | 1/40 | 3 | 2/40 | 5 |
| 10 | 39/40 | 98 | 34/40 | 85 |
| 30 | 39/40 | 98 | 39/40 | 98 |

These results indicate that DTI-100 can induce "on demand" (in response to drug application), "rapid onset" (within 1-3 minutes), "rapid offset" (complete within 5-10 minutes) voiding of urine and/or feces. The observed voiding responses occurred in a defined dose range, were stable and consistent across multiple doses per day, and were stable across multiple days of dosing.

Example 10

Experiments in Rats and Dogs for Rapid-Onset, Short Duration NK2R Antagonists to Terminate the Actions of an NK2R Agonist The time to complete voiding after administration of an NK2R agonist can be independent of the NK2R agonist's duration of action because once the bladder or rectum is empty, voiding is complete despite continued activation of the NK2R by the agonist. Thus, an NK2R antagonist that can reduce smooth muscle prokinetic effects due to the agonist, with an onset of action that occurs substantially after voiding is complete, and a duration of action that is longer than that of the NK2R agonist but shorter than the interval at which a subject would want to void again can be of therapeutic benefit.

Described below are methods to determine the efficacy, onset of action, and duration of action of NK2R antagonists with therapeutic benefit to reverse the unwanted effects of an NK2R agonist administered to induce voiding. It is generally understood by those of skill in the art, modifying the structure of known NK2R antagonists can allow for alteration of pharmacokinetic properties to increase or decrease duration of action and/or to reduce penetration into the CNS. The following methods are used to determine the efficacy, onset of action and the duration of action of various compounds that demonstrate NK2R antagonist properties on the prokinetic actions of NKR agonists on bladder and gastrointestinal (GI) function in rats and dogs. In addition, the reproducibility of multiple dosing and the pharmacodynamic (PD) responses of administering the NK2R antagonists via various routes of administration are explored. Further, the effects of NK2R antagonists on adverse events after administration of an NK2R agonist to beagle dogs are investigated. In summary, the efficacy, onset of action, and duration of action of NK2R antagonists to reverse NK2R agonist-induced increases in bladder and colorectal contractions and/or adverse events are described.

Rat Method:

General: In vivo studies are performed in anesthetized, acutely spinalized (T9-10 level) rats (N=37) or spinally intact (N=3) rats. Rats are housed with free access to water and food in a colony room that is maintained on a 12 hr/12 hr light/dark cycle 1-2 weeks before the experiment. Rats are anesthetized with urethane (1.2-1.4 g/kg subcutaneous injection). Surgical procedures are then performed with the addition of isoflurane anesthesia (0.05-1.5% in O2) as the full anesthetic effect of urethane takes about 1-2 hrs.

A catheter filled with heparinized saline (50 unit/ml) is inserted into the carotid artery and connected to a pressure transducer for measurement of blood pressure and heart rate. A catheter is inserted into the jugular vein for intravenous (i.v.) administration of drugs. In order to transect the spinal cord, the skin and muscle on the dorsal side at the level of the lower thoracic vertebrae are incised, and the spinal cord is carefully exposed by a laminectomy and transected at the T8-T10 spinal level. Gelfoam is placed at the incision site and the muscle and skin overlying the vertebrae are closed with wound clips. The spinal cord is cut at least 60 min before starting the experimental protocol. Blood pressure, bladder pressure and colorectal pressure signals are amplified and displayed on a computer using LABCHART (AD Instruments, Colorado Springs, Colo.).

Bladder Contractility: For isovolumetric recordings of bladder pressure a saline-filled polyethylene tubing with a flared tip (PE 50®) catheter is inserted into the bladder and secured in place at the dome. This catheter is used to slowly infuse saline (0.2-0.3 ml/min by an infusion pump (PHD2000 infusion, Harvard Apparatus, Holliston, Mass.) to determine the bladder capacity. The bladder capacity is determined as the volume necessary to fill the bladder to the leak point pressure (i.e. volume required to produce voiding). The bladder is then emptied, the external urethra occluded and the bladder filled to 70% capacity. This method produced a stable baseline pressure in which drug induced changes in bladder contractility could be measured. Peak pressure responses, time to peak, and time to return to near baseline values (within 5 mmHg of baseline; i.e. duration of action) after vehicle and drug administration are measured.

Colorectal Contractility: Colorectal pressures are measured via a latex balloon catheter (length 3-5 cm) inserted (~4 cm) into the distal rectal/colon region. The catheter is connected to a pressure monitoring system. The pressure in the balloon catheter is slowly increase to 15-20 mmHg by infusing saline (0.3-0.7 ml total volume) and this pressure is maintained throughout the study. This allowed drug induced changes in colorectal pressure to be monitored. Parameters measured include peak colorectal pressure response, duration of time above baseline activity (in the $1^{st}$ 5 min after drug administration), area under the curve (measured during the $1^{st}$ 5 min after drug administration) and the number of contractile events after vehicle and drug administration.

Dosing: To demonstrate utility of an NK2R antagonist to reverse activity of an NK2R agonist, the NK2R antagonist is administered during continuous infusion of an NK2R agonist while recording bladder or rectal pressure. For example, after establishing a steady-state elevation of bladder or rectal pressure (i.e. baseline pressure) using an intravenous infusion of NKA (or another NK2R agonist) at a rate of about 1-100 pm/kg/min, the NK2R antagonist is administered as an intravenous bolus. The efficacy of the NK2R antagonist is assessed by the magnitude of the reversal of the baseline pressure increase produced by NKA infusion (i.e. decrease in pressure from baseline). Onset of action of the NK2R antagonist is obtained by measuring the time from administration of the NK2R antagonist to the time when pressure is first significantly decreased (threshold onset of action) or to the time when the pressure is maximally decreased (onset of maximal action). The duration of action of the NK2R antagonist is obtained by measuring the time from its administration to the time when the NK2R antagonist-induced decrease in baseline pressure is no longer significant (i.e. the pressure returns to baseline pressure values recorded prior to NK2R antagonist administration).

Dog Methods:

General: Beagle dogs (6-11 kg, purpose-bred and experimentally naïve) are housed at an AAALAC approved facility in cages (1/cage) with access to water and food. A butterfly intravenous catheter is inserted into a vein (e.g. radial or saphenous). All animal activities are performed in compliance with USDA guidelines. Animals are monitored for 5 days prior to dosing to ensure adequate health.

Treatments and Dosing: Animals are administered a dose of an NK2R agonist that produces observed adverse events. For example, intravenous administration of 150 ug/kg of DTI-100 can produce voiding and defecation within minutes of administration, followed within minutes by retching, emesis, panting, and vocalization that last approximately 15 minutes. Adverse events are commonly quantified by measuring the number of events and the duration of each event occurring during "1 minute time bins" after NK2R agonist administration to create a time histogram of events. When voiding has stopped, a NK2R antagonist is administered intravenously. Efficacy of the NK2R antagonist is obtained by measuring the reduction in the number and duration of adverse events.

Onset of action of the NK2R antagonist is obtained by recording the minute time bin in which a significant reduction of adverse events occurs (threshold onset of action) and the minute time bin in which the adverse events are minimized by that dose (onset of maximal action). The duration of action is obtained by recording the minute time bin when adverse events return. It should be recognized that a duration of action of an NK2R antagonist that is longer than the duration of the NK2R agonist cannot be measured with this technique because no minute time bin will show a significant number of adverse events beyond the duration of action of the NK2R agonist. To determine the duration of action when the agonist duration of action is shorter than the antagonist, the antagonist is administered prior to administration of the agonist (i.e. pre-treatment), and the agonist is administered at various times (e.g. 30 min, 1 hr, 2 hr, 4 hr, 8 hour) after the antagonist. The maximal duration of action is obtained by recording the time interval at which the adverse events with pre-treatment equal the adverse events without pre-treatment. Since it is unlikely that a subject would want to utilize NK2R agonist-induced voiding at less than a 2 hour interval, antagonist pre-treatment is tested at intervals of greater than 2 hours.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference.

REFERENCES

Bushfield, M., M. Metcalfe and A. M. Naylor (1995). "Activation of the micturition reflex by NK2 receptor stimulation in the anaesthetized guinea-pig." Br J Pharmacol 115(6): 875-882.

Candenas, L., A. Lecci, F. M. Pinto, E. Patak, C. A. Maggi and J. N. Pennefather (2005). "Tachykinins and tachykinin receptors: effects in the genitourinary tract." Life Sci 76(8): 835-862.

Evans, T. W., C. M. Dixon, B. Clarke, T. B. Conradson and P. J. Barnes (1988). "Comparison of neurokinin A and substance P on cardiovascular and airway function in man." Br J Clin Pharmacol 25(2): 273-275.

Hallgren, A., G. Flemstrom, P. M. Hellstrom, M. Lordal, S. Hellgren and O. Nylander (1997). "Neurokinin A increases duodenal mucosal permeability, bicarbonate secretion, and fluid output in the rat." Am J Physiol 273(5 Pt 1): G1077-1086.

Kullmann, F. A., Zheng, J, Wells, G., McKenna, D., Burgard, E. and Thor, K. (2013) "Excitatory effects of neurokinin 2 and bombesin receptor peptide agonists vivo in urinary tract of rats with voiding dysfunctions." FASEB J 27: (Meeting Abstract Supplement) Ib862.

Lecci, A., A. Capriati, M. Altamura and C. A. Maggi (2006). "Tachykinins and tachykinin receptors in the gut, with special reference to NK2 receptors in human." Auton Neurosci 126-127: 232-249.

Lecci, A., S. Giuliani, R. Patacchini and C. A. Maggi (1993). "Evidence against a peripheral role of tachykinins in the initiation of micturition reflex in rats." J Pharmacol Exp Ther 264(3): 1327-1332.

Lordal, M., G. Navalesi, E. Theodorsson, C. A. Maggi and P. M. Hellstrom (2001). "A novel tachykinin NK2 receptor antagonist prevents motility-stimulating effects of neurokinin A in small intestine." Br J Pharmacol 134(1): 215-223.

Lordal, M., E. Theodorsson and P. M. Hellstrom (1997). "Tachykinins influence interdigestive rhythm and contractile strength of human small intestine." Dig Dis Sci 42(9): 1940-1949.

Maggi, C. A., S. Giuliani, P. Santicioli, L. Abelli, D. Regoli and A. Meli (1987). "Further studies on the mechanisms of the tachykinin-induced activation of micturition reflex in rats: evidence for the involvement of the capsaicin-sensitive bladder mechanoreceptors." Eur J Pharmacol 136(2): 189-205.

Maggi, C. A., R. Patacchini, S. Giuliani and A. Giachetti (1993). "In vivo and in vitro pharmacology of SR 48,968, a non-peptide tachykinin NK2 receptor antagonist." Eur J Pharmacol 234(1): 83-90.

Maggi, C. A., P. Santicioli, S. Giuliani, D. Regoli and A. Meli (1986). "Activation of micturition reflex by substance P and substance K: indirect evidence for the existence of multiple tachykinin receptors in the rat urinary bladder." J Pharmacol Exp Ther 238(1): 259-266.

Martling, C. R., E. Theodorsson-Norheim, I. Norheim and J. M. Lundberg (1987). "Bronchoconstrictor and hypotensive effects in relation to pharmacokinetics of tachykinins in the guinea-pig—evidence for extraneuronal cleavage of neuropeptide K to neurokinin A." Naunyn Schmiedebergs Arch Pharmacol 336(2): 183-189.

Matuszek, M. A., X. P. Zeng, J. Strigas and E. Burcher (1998). "An investigation of tachykinin NK2 receptor subtypes in the rat." Eur J Pharmacol 352(1): 103-109.

Palea, S., M. Corsi, W. Artibani, E. Ostardo and C. Pietra (1996). "Pharmacological characterization of tachykinin NK2 receptors on isolated human urinary bladder, prostatic urethra and prostate." J Pharmacol Exp Ther 277(2): 700-705.

Schmidt, P. T., M. Lordal, B. Gazelius and P. M. Hellstrom (2003). "Tachykinins potently stimulate human small bowel blood flow: a laser Doppler flowmetry study in humans." Gut 52(1): 53-56.

Severini, C., G. Improta, G. Falconieri-Erspamer, S. Salvadori and V. Erspamer (2002). "The tachykinin peptide family." Pharmacol Rev 54(2): 285-322.

Tanaka, T., S. Matsumoto-Okano, N. Inatomi, Y. Fujioka, H. Kamiguchi, M. Yamaguchi, A. Imanishi, M. Kawamoto, K. Miura, Y. Nishikawa and Y. Tsukimi (2012). "Establishment and validation of a rabbit model for in vivo pharmacodynamic screening of tachykinin NK2 antagonists." J Pharmacol Sci 118(4): 487-495.

Taylor, J. A., 3rd and G. A. Kuchel (2006). "Detrusor underactivity: Clinical features and pathogenesis of an underdiagnosed geriatric condition." J Am Geriatr Soc 54(12): 1920-1932.

Tramontana, M., R. Patacchini, A. Lecci, S. Giuliani and C. A. Maggi (1998). "Tachykinin NK2 receptors in the hamster urinary bladder: in vitro and in vivo characterization." Naunyn Schmiedebergs Arch Pharmacol 358(3): 293-300.

Warner, F. J., R. C. Miller and E. Burcher (2002). "Structure-activity relationship of neurokinin A(4-10) at the human tachykinin NK(2) receptor: the effect of amino acid substitutions on receptor affinity and function." Biochem Pharmacol 63(12): 2181-2186.

Warner, F. J., R. C. Miller and E. Burcher (2003). "Human tachykinin NK2 receptor: a comparative study of the colon and urinary bladder." Clin Exp Pharmacol Physiol 30(9): 632-639.

Zeng, X. P., K. H. Moore and E. Burcher (1995). "Characterization of tachykinin NK2 receptors in human urinary bladder." J Urol 153(5): 1688-1692.

One skilled in the art will readily appreciate that the presently described subject matter is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the invention as defined by the scope of the claims.

That which is claimed:

1. A method for inducing one or both of urinary voiding and defecation in a mammal, which comprises administering on an as-needed basis to the mammal a therapeutically effective amount of a neurokinin 2 receptor (NK2R) agonist also having selectivity over neurokinin 1 (NK1R) and neurokinin 3 (NK3R) receptors, wherein the NK2R agonist is a NKA analogue, or a pharmaceutically acceptable salt thereof formulated as an immediate release dosage form, wherein the administering is by a mode selected from the group consisting of transmucosal, intramuscular, and subcutaneous, wherein the NK2R agonist or the pharmaceutically acceptable salt thereof, has a rapid onset and a short duration of action, to induce the as-needed one or both of urinary voiding and defecation.

2. A method for inducing one or both of urinary voiding and defecation in a mammal, which comprises administering on an as-needed basis to the mammal a therapeutically effective amount of [Lys5,MeLeu9,Nle10]-NKA(4-10) (SEQ ID NO: 1), or a pharmaceutically acceptable salt thereof, formulated as an immediate release dosage form, wherein the administering is by a mode selected from the group consisting of transmucosal, intramuscular, and subcutaneous, to induce the as-needed one or both of urinary voiding and defecation.

3. The method of claim 1, wherein the transmucosal administering comprises transbuccal, lingual, sublingual, inhalation, intranasal, topical, transrectal, or transurethral.

4. The method of claim 3, wherein the lingual administering comprises a rapidly disintegrating tablet.

5. The method of claim 1, wherein the mammal is a human, a cat, or a dog.

6. The method of claim 1, wherein the rapid-onset is characterized by a $T_{max}$ up to about 10 minutes after NK2R agonist administration.

7. The method of claim 1, wherein the rapid-onset is characterized by a $T_{max}$ up to about 5 min after NK2R agonist administration.

8. The method of claim 1, wherein the short duration of action is characterized by a $T_{1/2}$ ranging from about 1 hour to about 10 minutes after NK2R agonist administration.

9. The method of claim 1, wherein the short duration of action is characterized by a $T_{1/2}$ ranging from about 30 minutes to about 10 minutes after NK2R agonist administration.

10. The method of claim 1, wherein the short duration of action is characterized by a $T_{1/2}$ ranging from about 15 minutes to about 1 minute after NK2R agonist administration.

11. The method of claim 1, wherein the as-needed administering is up to about 5 minutes prior to when the voiding and/or defecation is desired.

12. The method of claim 1, wherein the as-needed administering is up to about 10 minutes prior to when the voiding and/or defecation is desired.

13. The method of claim 1, wherein the as-needed administering is repeated multiple times per day.

14. The method of claim 1, further comprising administering a therapeutically effective amount of a NK2R antagonist, or a pharmaceutically acceptable salt thereof, to terminate at least a majority of the effects of the NK2R agonist, wherein the NK2R antagonist has a duration of action of less than about 4 hours.

15. A method for treating one of urinary voiding and defecation dysfunction in a mammal in need of treatment, which comprises administering on an as-needed basis to the mammal a therapeutically effective amount of an neurokinin 2 receptor (NK2R) agonist also having selectivity over a neurokinin 1 receptor (NK1R) and a neurokinin 3 receptor (NK3R), wherein the NK2R agonist is a NKA analogue, or a pharmaceutically acceptable salt thereof formulated as an immediate release dosage form, wherein the administering is by a mode selected from the group consisting of transmucosal, intramuscular, and subcutaneous, wherein the NK2R agonist or the pharmaceutically acceptable salt thereof, has a rapid onset and a short duration of action, to induce the as-needed one or both of urinary voiding and defecation.

16. The method of claim 15, wherein the one of voiding and defecation dysfunction is a result of one of spinal cord injury, traumatic brain injury, multiple sclerosis, spina bifida, degenerative brain disease, Alzheimer's, Parkinson's, dementia, diabetes, advanced age, or postoperative status, and combinations thereof.

17. The method of claim 15, wherein the NKA analogue is [Lys5,MeLeu9,Nle10]-NKA(4-10) (SEQ ID NO: 1).

18. The method of claim 15, wherein the transmucosal administering comprises transbuccal, lingual, sublingual, inhalation, intranasal, topical, transrectal, or transurethral.

19. The method of claim 18, wherein the lingual administering comprises a rapidly disintegrating tablet.

20. The method of claim 15, wherein the mammal is a human, a cat, or a dog.

21. The method of claim 15, wherein the rapid-onset is characterized by a $T_{max}$ up to about 10 minutes after NK2R agonist administration.

22. The method of claim 15, wherein the short duration of action is characterized by a $T_{1/2}$ ranging from about 1 hour to about 10 minutes after NK2R agonist administration.

23. The method of claim 15, wherein the as-needed administering is up to about 10 minutes prior to when the voiding and/or defecation is desired.

24. The method of claim 15, wherein the as-needed administering is repeated multiple times per day.

25. The method of claim 1, wherein the NKA analogue is selected from the group consisting of NKA(4-10)) (SEQ ID NO: 5), [Lys5,MeLeu9,Nle10]-NKA(4-10) (SEQ ID NO: 1), [βAla8]NKA(4-10) (SEQ ID NO: 6), and GR 64349.

26. The method of claim 15, wherein the NKA analogue is selected from the group consisting of NKA(4-10)) (SEQ ID NO: 5), [Lys5,MeLeu9,Nle10]-NKA(4-10) (SEQ ID NO: 1), [βAla8]NKA(4-10) (SEQ ID NO: 6), and GR 64349.

* * * * *